US011007163B2

(12) United States Patent
Huang et al.

(10) Patent No.: US 11,007,163 B2
(45) **Date of Patent: *May 18, 2021**

(54) GLUTARATE COMPOUNDS FOR TREATING ISCHEMIA-REPERFUSION INJURIES

(71) Applicant: The Regents of the University of California, Oakland, CA (US)

(72) Inventors: Jing Huang, Los Angeles, CA (US); Xudong Fu, Los Angeles, CA (US); Xiang Yin, Los Angeles, CA (US); Mansoureh Eghbali, Los Angeles, CA (US); Jingyuan Li, San Diego, CA (US); Karen Lynn Reue, Torrance, CA (US); Laurent Vergnes, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/673,081

(22) Filed: Nov. 4, 2019

(65) Prior Publication Data

US 2020/0069621 A1 Mar. 5, 2020

Related U.S. Application Data

(63) Continuation of application No. 16/297,599, filed on Mar. 9, 2019, now Pat. No. 10,500,177, which is a continuation of application No. 15/582,748, filed on Apr. 30, 2017, now Pat. No. 10,285,962.

(60) Provisional application No. 62/330,178, filed on May 1, 2016.

(51) Int. Cl.

| | |
|---|---|
| ***A61K 31/194*** | (2006.01) |
| ***A61K 31/616*** | (2006.01) |
| ***A61K 31/365*** | (2006.01) |
| ***A61K 31/198*** | (2006.01) |

(52) U.S. Cl.

CPC .......... *A61K 31/194* (2013.01); *A61K 31/198* (2013.01); *A61K 31/365* (2013.01); *A61K 31/616* (2013.01)

(58) Field of Classification Search

CPC .. A61K 31/194; A61K 31/198; A61K 31/365; A61K 31/616

USPC .......................................................... 514/161

See application file for complete search history.

(56) References Cited

U.S. PATENT DOCUMENTS

| | | | | |
|---|---|---|---|---|
| 10,285,962 | B2 * | 5/2019 | Huang ................ | A61K 31/194 |
| 10,500,177 | B2 * | 12/2019 | Huang ................ | A61K 31/198 |
| 2011/0300237 | A1 | 12/2011 | De Groot et al. | |
| 2017/0333373 | A1 | 11/2017 | Huang et al. | |

FOREIGN PATENT DOCUMENTS

| | | | |
|---|---|---|---|
| CN | 101579331 | A | 11/2009 |
| WO | 1995034301 | A1 | 12/1995 |

OTHER PUBLICATIONS

Extended European Search report received in EP17793057, dated Dec. 6, 2019.

International Search Report received in PCT/US2017/030320, dated Aug. 4, 2017.

Written Opinion received in PCT/US2017/030320, dated Aug. 4, 2017.

Cayman Chemical, "Safety Data Sheet, .alpha.-Hydroxyglutaric acid (sodium salt)", Nov. 12, 2014, Publisher: https:/fwww.caymanchem.com/msdss/16374m.pdf.

Goncalves, et al., "Effect of short-term ornithine alpha-ketoglutarate pretreatment on intestinal ischemia-reperfusion in rats", 2011, pp. 2-7, vol. 26, Number Suppl. 1, Publisher: Acta Cirurgica Brasileira.

Oldham, et al., "Hypoxia-mediated Increases in L-2-hydroxyglutarate Coordinate the Metabolic Response to Reductive Stress", Jul. 23, 2015, pp. 291-303, vol. 22, No. 2, Publisher: Cell Metab.

* cited by examiner

*Primary Examiner* — Kristin A Vajda

(74) *Attorney, Agent, or Firm* — Suzannah K. Sundby, Esq.; Canady + Lortz LLP

(57) ABSTRACT

Disclosed herein are methods of preventing, inhibiting, reducing, or treating ischemia and reperfusion injury to tissues with glutarate compounds such as α-ketoglutarate.

20 Claims, 6 Drawing Sheets
(5 of 6 Drawing Sheet(s) Filed in Color)

GLUTARATE COMPOUNDS FOR TREATING ISCHEMIA-REPERFUSION INJURIES

ACKNOWLEDGEMENT OF GOVERNMENT SUPPORT

This invention was made with Government support under AT006889 and HL119886, awarded by the National Institutes of Health. The Government has certain rights in the invention.

BACKGROUND OF THE INVENTION

1. Field of the Invention

The present invention relates to treating ischemia-reperfusion injuries.

2. Description of the Related Art

Ischemia-reperfusion injury is a common clinical problem, whether resulting from spontaneous events (such as heart attack and stroke) or induced artificially during surgery and organ transplantation. Standard declotting and antiplatelet treatments as part of the reperfusion procedure aim to save the life of the patient, but do not address the debilitating tissue/organ damage caused by ischemia and/or reperfusion. Ischemia-reperfusion injuries are the leading cause of morbidity and mortality after such events.

Therefore, a need exists for treatments for ischemia-reperfusion injuries.

SUMMARY OF THE INVENTION

In some embodiments, the present invention is a method of preventing, inhibiting, reducing, or treating an ischemia-reperfusion injury (IR injury) to a tissue in or of a subject, which comprises administering to the tissue or the subject a therapeutically effective amount of at least one glutarate compound before, during, and/or after an event that causes an IR injury. In some embodiments, at least one glutarate compound is a compound of Formula I or Formula II as disclosed herein. In some embodiments, the at least one glutarate compound is an α-KG compound or a 2-HG compound as disclosed herein. In some embodiments, the at least one glutarate compound is α-ketoglutarate (α-KG), 2-hydroxyglutaric acid, and/or (S)-2-hydroxyglutaric acid (S-2HG). In some embodiments, the at least one glutarate compound is administered in the form of a pharmaceutical composition. In some embodiments, the pharmaceutical composition comprises a pharmaceutically acceptable carrier. In some embodiments, the at least one glutarate compound is administered within 1 to 2 hours of the event that causes an IR injury. In some embodiments, the at least one glutarate compound is administered within 1 hour of the event that causes an IR injury. In some embodiments, the at least one glutarate compound is administered within 30 minutes of the event that causes an IR injury. In some embodiments, the at least one glutarate compound is administered during the event that causes an IR injury. In some embodiments, the at least one glutarate compound is administered immediately prior to the event that causes an IR injury. In some embodiments, the glutarate compound is administered after the event that causes an IR injury. In some embodiments, the therapeutically effective amount is administered as a single dose. In some embodiments, the therapeutically effective amount is about 5-20 mg/kg or about 10-15 mg/kg weight of the subject. In some embodiments, the at least one glutarate compound is an α-KG compound, and the therapeutically effective amount is about 5-15 mg/kg, about 10-15 mg/kg, or about 11-12 mg/kg weight of the subject. In some embodiments, the at least one glutarate compound is a 2-HG compound, and the therapeutically effective amount is about 10-20 mg/kg, about 15-20 mg/kg, or about 15-16 mg/kg weight of the subject. In some embodiments, the at least one glutarate compound is administered directly to the tissue in vivo, for example, to cardiac tissue during surgery on the heart. In some embodiments, the at least one glutarate compound is administered directly to the tissue ex vivo, for example, by preserving, flushing, or reperfusing the tissue with a fluid, such as preservation fluid, flush fluid, or reperfusion fluid used in organ transplantations, that comprises the at least one glutarate compound. In some embodiments, the tissue is cardiac tissue. In some embodiments, the tissue is an organ. In some embodiments, the organ is a heart, liver, lung, kidney, or the like. In some embodiments, the event that causes an IR injury is ischemia, reperfusion, thromboembolism, vasoconstriction, cardiac standstill, myocardial infarction, stroke, or surgery. In some embodiments, the event is a myocardial infarction.

In some embodiments, the present invention is a method of treating or reducing an ischemia-reperfusion injury (IR injury) to a tissue in or of a subject, which comprises administering to the tissue or the subject a pharmaceutical composition comprising a therapeutically effective amount of a compound of Formula I:

(I)

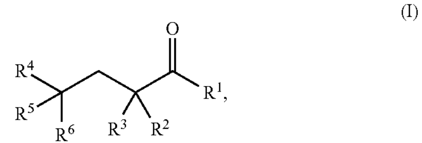

wherein $R^1$ is hydrogen, halogen, —CHO, —$OR^7$, —$NR^8R^9$, —$COOR^7$, —$CONR^8R^9$, —$SR^{10}$, substituted or unsubstituted alkyl, or substituted or unsubstituted heteroalkyl; $R^2$ and $R^3$ are each independently hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl; or $R^2$ and $R^3$, together with the atom to which they are bound, form an oxo; $R^4$ and $R^5$ are each independently hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl; $R^6$ is halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl; and $R^7$, $R^8$, $R^9$, and $R^{10}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a salt thereof. In some embodiments, $R^1$ is hydrogen, —CHO, or —$OR^7$. In some embodiments, $R^1$ is —$OR^7$, wherein $R^7$ is hydrogen, substituted or unsubstituted alkyl, or substituted or unsubstituted aryl. In some embodiments, $R^1$ is —$OR^7$, wherein $R^7$ is $C_{1-20}$ substituted or unsubstituted alkyl. In some embodiments, $R^2$ is hydrogen, halogen, —CN, —CHO, or —$NR^8R^9$, wherein $R^8$ and $R^9$ are each independently hydrogen or substituted or unsubstituted alkyl. In some embodiments, $R^2$ and $R^3$, together with the atom to which they are bound, form an oxo. In some embodiments, $R^4$ and $R^5$ are each independently hydrogen, —CHO, —$OR^7$, —$NR^8R^9$, —$COOR^7$, or —$CONR^8R^9$, wherein $R^7$, $R^8$, and $R^9$ are each independently hydrogen or $C_{1-20}$ substituted or unsubstituted alkyl. In some embodiments, $R^6$ is —CHO, —$OR^7$, —$NR^8R^9$, —$COOR^7$, or —$CONR^8R^9$, wherein $R^7$, $R^8$, and $R^9$ are each independently hydrogen or $C_{1-20}$ substituted or unsubstituted alkyl. In some embodiments, $R^6$ is —$COOR^7$ or —$CONR^8R^9$, wherein $R^7$, $R^8$, and $R^9$ are each independently hydrogen or $C_{1-20}$ substituted or unsubstituted alkyl. In some embodiments, the compound is alpha-ketoglutaric acid (α-KG). In some embodiments, the compound is dimethyl 2-oxoglutarate. In some embodiments, the compound is a 2-HG compound. In some embodiments, the compound is 2-hydroxyglutaric acid. In some embodiments, the compound is (S)-2-hydroxyglutaric acid (S-2HG). In some embodiments, the compound is administered during an event that causes an IR injury. In some embodiments, the compound is administered after the event that causes an IR injury. In some embodiments, the compound is administered within 1 to 2 hours of the event. In some embodiments, the compound is administered within 1 hour of the event. In some embodiments, the compound is administered within 30 minutes, 25 minutes, 20 minutes, 15 minutes, 10 minutes, or 5 minutes of the event. In some embodiments, the compound is administered as a single dose. In some embodiments, the therapeutically effective amount is about 5-20 mg/kg, or about 10-15 mg/kg weight of the subject. In some embodiments, the compound is administered to the subject in combination with an additional therapeutic agent. In some embodiments, the additional therapeutic agent is oligomycin. In some embodiments, the additional therapeutic agent is aspirin. In some embodiments, the event is a myocardial infarction. In some embodiments, the tissue is cardiac tissue.

In some embodiments, the present invention is a method of preventing or inhibiting an ischemia-reperfusion injury (IR injury) to a tissue in or of a subject, which comprises administering to the tissue or the subject pharmaceutical composition comprising a therapeutically effective amount of a compound of Formula I:

(I)

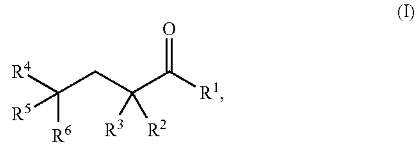

wherein $R^1$ is hydrogen, halogen, —CHO, —$OR^7$, —$NR^8R^9$, —$COOR^7$, —$CONR^8R^9$, —$SR^{10}$, substituted or unsubstituted alkyl, or substituted or unsubstituted heteroalkyl; $R^2$ and $R^3$ are each independently hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl; or $R^2$ and $R^3$, together with the atom to which they are bound, form an oxo; $R^4$ and $R^5$ are each independently hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl; $R^6$ is halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl; and $R^7$, $R^8$, $R^9$, and $R^{10}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a salt thereof; and an excipient. In some embodiments, $R^1$ is hydrogen, —CHO, or —$OR^7$. In some embodiments, $R^1$ is —$OR^7$, wherein $R^7$ is hydrogen, substituted or unsubstituted alkyl, or substituted or unsubstituted aryl. In some embodiments, $R^1$ is —$OR^7$, wherein $R^7$ is $C_{1-20}$ substituted or unsubstituted alkyl. In some embodiments, $R^2$ is hydrogen, halogen, —CN, —CHO, or —$NR^8R^9$, wherein $R^8$ and $R^9$ are each independently hydrogen or substituted or unsubstituted alkyl. In some embodiments, $R^2$ and $R^3$, together with the atom to which they are bound, form an oxo. In some embodiments, $R^4$ and $R^5$ are each independently hydrogen, —CHO, —$OR^7$, —$NR^8R^9$, —$COOR^7$, or —$CONR^8R^9$, wherein $R^7$, $R^8$, and $R^9$ are each independently hydrogen or $C_{1-20}$ substituted or unsubstituted alkyl. In some embodiments, $R^6$ is —$NR^8R^9$, —$COOR^7$, —$CONR^8R^9$, wherein $R^7$, $R^8$, and $R^9$ are each independently hydrogen or $C_{1-20}$ substituted or unsubstituted alkyl. In some embodiments, $R^4$ is —$COOR^7$ or —$CONR^8R^9$, wherein $R^7$, $R^8$, and $R^9$ are each independently hydrogen or $C_{1-20}$ substituted or unsubstituted alkyl. In some embodiments, $R^6$ is —$COOR^7$, wherein $R^7$ is hydrogen. In some embodiments, the compound is alpha-ketoglutarate (α-KG). In some embodiments, the compound is a 2-HG compound. In some embodiments, the compound is disodium (S)-2-hydroxyglutarate (S-2HG). In some embodiments, the compound is administered prior to an event that causes an IR injury. In some embodiments, the compound is administered as a single dose. In some embodiments, the therapeutically effective amount is about 5-20 mg/kg, or about 10-15 mg/kg weight of the subject. In some embodiments, the tissue is cardiac tissue.

In some embodiments, the present invention is a method of increasing cyclophilin D (CypD)-Complex V formation in a cell, which comprises contacting a cell with at least one glutarate compound. In some embodiments, at least one glutarate compound is a compound of Formula I or Formula II as disclosed herein. In some embodiments, the at least one glutarate compound is an α-KG compound or a 2-HG compound as disclosed herein. In some embodiments, the at least one glutarate compound is α-ketoglutarate (α-KG), 2-hydroxyglutaric acid, dimethyl 2-oxoglutarate, and/or (S)-2-hydroxyglutaric acid (S-2HG). In some embodiments, the increase in cyclophilin D-Complex V formation is relative to a control, e.g., the formation of CypD and Complex V of an equivalent cell in the absence of the at least one glutarate compound. In some embodiments, the cell is from a cardiac tissue. In some embodiments, the cell is from a mammalian cardiac tissue. In some embodiments, the cell is from a human cardiac tissue.

In some embodiments, the present invention is directed to the use of at least one glutarate compound in the manufacture of a medicament for preventing, inhibiting, reducing, or treating an ischemia-reperfusion injury (IR injury) to a tissue in or of a subject. In some embodiments, the present invention is directed to the use of at least one glutarate compound for the manufacture of a medicament for preventing, inhibiting, reducing, or treating an ischemia-reperfusion injury (IR injury), wherein the medicament is prepared to be administered in accordance with one or more of the dosage regimens as described herein, e.g., paragraphs [0010], [0052], and [0055]. In some embodiments, the medicament comprises a therapeutically effective amount of the at least one glutarate compound. In some embodiments, the at least one glutarate compound is a compound of Formula I or Formula II as disclosed herein. In some embodiments, the at least one glutarate compound is an α-KG compound or a 2-HG compound as disclosed herein. In some embodiments, the at least one glutarate compound is α-ketoglutarate (α-KG), 2-hydroxyglutaric acid, and/or (S)-2-hydroxyglutaric acid (S-2HG). In some embodiments, the medicament comprises a pharmaceutically acceptable carrier.

In some embodiments, the subject of the methods of the present invention is a mammalian subject. In some embodiments, the subject is a human subject. In some embodiments, the subject is one who is in need of treatment with at least one glutarate compound. As used herein, a subject who is in need of treatment with at least one glutarate compound is one who has, will, or will likely experience an event that causes an IR injury. In some embodiments, the at least one glutarate compound to be administered to the subject is exogenous to the subject. In some embodiments, the compositions comprise a concentrated amount of at least one glutarate compound, wherein the concentrated amount is a concentration that is higher than naturally occurring concentrations of the at least one glutarate compound or its naturally occurring counterpart as found in nature.

The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

The patent or application file contains at least one drawing executed in color.

Copies of this patent or patent application publication with color drawing(s) will be provided by the Office upon request and payment of the necessary fee. This invention is further understood by reference to the drawings wherein:

FIG. 1 provides the structure of α-KG and schematically shows the experimental protocol. Isolated, Langendorff hearts from mice were perfused with Krebs Henseleit buffer (KH) and after stabilization subjected to ischemia for 30 minutes. After ischemia, hearts were perfused with KH, control (CTRL), or α-KG (800 μM) for 60 minutes.

FIG. 2 and FIG. 3 are representative graphs of the left ventricular developed pressure (LVDP) and $dP/dt_{Max}$ and $dP/dt_{Min}$ as a function of time for controls (hearts perfused with KH) (FIG. 2) and hearts perfused with α-KG (FIG. 3).

FIG. 4 is a graph showing left ventricular developed pressure (LVDP) as a function of time.

FIG. 5 is a graph showing rate pressure product (RPP) as a function of time.

FIG. 6 is a graph showing the maximum rate of left ventricle (LV) pressure rise ($dP/dt_{max}$) as a function of time. *$p<0.05$.

FIG. 7 schematically shows the experimental protocol. The LAD was occluded for 45 minutes followed by 24 hours of reperfusion. One single IV bolus of phosphate buffered saline (PBS) (water as vehicle), α-KG (800 μM final in blood), or oligomycin (10 nM final in blood) was administered at reperfusion.

FIG. 8 are representative triphenyl tetrazolium chloride (TTC) stained cross-section of the heart. Infarcted tissue is white, the rest of the area at risk is red, and non-risk tissue is dark blue.

FIG. 9 is a graph showing the quantification of myocardial infarct size. Data show results of 4-5 biological replicates. Bars indicate mean±SEM. **$P<0.0001$, $P=0.0012$, NS (not significant), by unpaired t-test, two-tailed, two-sample unequal variance.

FIG. 10 is a graph showing the inhibition of heart ATP synthase by α-KG. α-KG decreases state 3 (initiated by 2 mM ADP), but not state 4o (oligomycin insensitive, that is, complex V independent) or 3u (FCCP-uncoupled maximal respiratory capacity), respiration in mitochondria isolated from mouse heart. Oligo, oligomycin; FCCP, carbonyl cyanide-4-(trifluoromethoxy)phenylhydrazone; AA, antimycin A. In the graph, the high data points in State 3 and State 3u are Vehicle.

FIG. 11 is a graph showing that α-KG does not affect the electron flow through the ETC. Oxygen consumption rate (OCR) from isolated mouse heart mitochondria at basal (pyruvate and malate as Complex I substrates, in presence of FCCP) and in response to sequential injection of rotenone (Rote; Complex I inhibitor), succinate (Complex II substrate), antimycin A (AA; complex III inhibitor), tetramethylphenylenediamine (TMPD; cytochrome c (Complex IV) substrate). No difference in Complex I (C I), Complex II (C II), or Complex IV (C IV) respiration is detected. In the graph, the high data points in State C II are Vehicle.

DETAILED DESCRIPTION OF THE INVENTION

Figure 1:
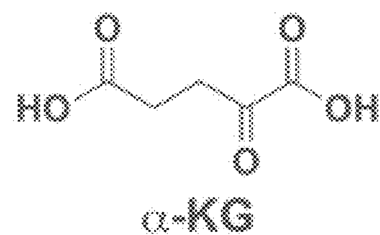
FIG. 1, FIG. 2, FIG. 3, FIG. 4, FIG. 5, and FIG. 6 show that administration of α-KG at reperfusion improves heart functional recovery in ex vivo mouse model.
Figure 1:
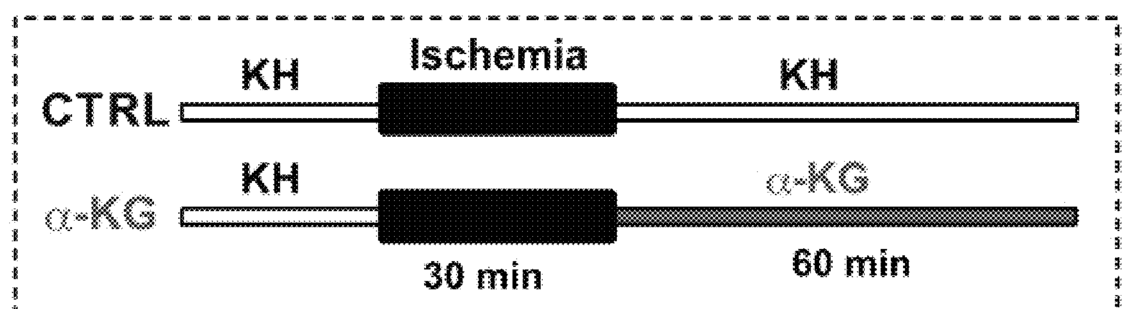

Ischemia or ischaemia is a restriction in blood supply to tissues, caused by a shortage of oxygen and glucose for cellular metabolism. Reperfusion (or reoxygenation) injury describes tissue damage caused by a return of blood to the tissue after a period of ischemia, anoxia, or hypoxia.

Because the drastic metabolic imbalance incurred by hypoxia, and that which results from the resupply of oxygen and nutrients upon reperfusion, impose severe stresses on the myocardium, the heart was used as a model for IR injury. Since all IR injuries are the result of ischemic and/or reperfusion conditions, these experiments and results using the heart as a model can be applied to other tissues and organs that are susceptible to IR injury, including brain, liver, kidney, and lung tissues.

As used herein, the term "ischemia-reperfusion injury" (IR injury) refers to tissue damage caused by ischemia, reperfusion, or ischemia followed by reperfusion. Thus, the term "IR injury" includes injuries caused by ischemia, reperfusion injuries, and injuries caused by ischemia followed by reperfusion. As used herein, an "event that causes an IR injury" includes ischemia, reperfusion, thromboembolism, vasoconstriction, cardiac standstill, myocardial infarction, stroke, surgeries in which blood flow to a tissue is prevented or reduced (e.g., organ transplantations, heart surgery, etc.), and the like. Myocardial infarction (MI) is a type of cardiac ischemia that can result in IR injury of the heart tissues.

Endogenous metabolites (including normal as well as aberrant disease-associated metabolites) were screened for their potential effects against heart IR injury using ex vivo and in vivo mouse models. From the screen, the tricarboxylic acid (TCA) cycle intermediate α-ketoglutarate (α-KG) was found to confer the greatest protection. In fact, one single bolus of α-KG at the onset of reperfusion reduced the infarct size in mice by about 70%. As disclosed herein, α-KG is a powerful therapeutic agent that can be used to rapidly restore heart function and reduce infarct size resulting from ischemia and/or reperfusion, caused by, for example, myocardial infarction. Thus, the present invention is directed to preventing, inhibiting, reducing, or treating IR injury to a tissue in a subject, which comprises administering to the subject a therapeutically effective amount of a glutarate compound, such as α-KG.

As used herein, a "glutarate compound" refers to α-KG compounds, 2-HG compounds, and compounds having the following Formula I:

(I)

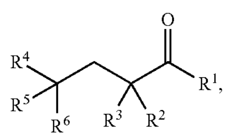

wherein $R^1$ is hydrogen, halogen, —CHO, —$OR^7$, —$NR^8R^9$, —$COOR^7$, —$CONR^8R^9$, —$SR^{10}$, substituted or unsubstituted alkyl, or substituted or unsubstituted heteroalkyl;

$R^2$ and $R^3$ are each independently hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl; or $R^2$ and $R^3$, together with the atom to which they are bound, form an oxo; and $R^4$, $R^5$, and $R^6$ are each independently hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl, wherein $R^7$, $R^8$, $R^9$, and $R^{10}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, and pharmaceutically acceptable solvates, salts, prodrugs, and metabolites thereof.

In some embodiments, $R^1$ is hydrogen, halogen, —CHO, —$OR^7$, —$NR^8R^9$, —$COOR^7$, —$CONR^8R^9$, or —$SR^{10}$. In some embodiments, $R^1$ is hydrogen, —CHO, or —$OR^7$. In some embodiments, $R^1$ is —$OR^7$, wherein $R^7$ is hydrogen, substituted or unsubstituted alkyl, or substituted or unsubstituted aryl. In some embodiments, $R^1$ is —$OR^7$, wherein $R^7$ is $C_{1-20}$ substituted or unsubstituted alkyl.

In some embodiments, $R^2$ and $R^3$ are each independently hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl. In some embodiments, $R^2$ and $R^3$ are each independently hydrogen, halogen, —CN, —CHO, or —$NR^8R^9$, wherein $R^8$ and $R^9$ are each independently hydrogen or substituted or unsubstituted alkyl. In some embodiments, $R^2$ and $R^3$, together with the atom to which they are bound, form an oxo.

In some embodiments, $R^4$, $R^5$, and $R^6$ are each independently hydrogen, —CHO, —$OR^7$, —$NR^8R^9$, —$COOR^7$, or —$CONR^8R^9$. In some embodiments, $R^4$, $R^5$, and $R^6$ are each independently hydrogen, halogen, —$OR^7$, —$NR^8R^9$, —$COOR^7$, —$CONR^8R^9$, or substituted or unsubstituted alkyl. In some embodiments, $R^4$ and $R^5$ are each independently hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl; and $R^6$ is halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl. In some embodiments, $R^4$ and $R^5$ are each independently hydrogen, —CHO, —$OR^7$, —$NR^8R^9$, —$COOR^7$, or —$CONR^8R^9$; and $R^6$ is —CHO, —$OR^7$, —$NR^8R^9$, —$COOR^7$, or —$CONR^8R^9$.

In some embodiments, $R^1$ is —$OR^7$ or —$NR^8R^9$; $R^2$ and $R^3$ are each independently hydrogen, —CHO, —$OR^7$, —$NR^8R^9$, or unsubstituted alkyl, or $R^2$ and $R^3$, together with the atom to which they are bound, form an oxo; $R^4$ and $R^5$ are each independently hydrogen, —$OR^7$, —$NR^8R^9$, or unsubstituted alkyl; $R^6$ is —$NR^8R^9$, —$COOR^7$, or —$CONR^8R^9$, and $R^7$, $R^8$, $R^9$, and $R^{10}$ are each independently hydrogen, or substituted or unsubstituted alkyl.

In some embodiments, $R^1$ is —$OR^7$ or —$NR^8R^9$; $R^2$ and $R^3$ are each independently hydrogen, —CHO, —$OR^7$, —$NR^8R^9$, or unsubstituted alkyl, or $R^2$ and $R^3$, together with the atom to which they are bound, form an oxo; $R^4$, $R^5$, and $R^6$ are each independently hydrogen, —$OR^7$, —$NR^8R^9$, or unsubstituted alkyl; and $R^7$, $R^8$, $R^9$, and $R^{10}$ are each independently hydrogen, or substituted or unsubstituted alkyl.

In some embodiments, $R^1$ is —$OR^7$; $R^2$ and $R^3$, together with the atom to which they are bound, form an oxo; $R^4$ and $R^5$ are each independently hydrogen or unsubstituted alkyl; $R^6$ is —$COOR^7$, $R^7$ is hydrogen; and $R^8$, $R^9$, and $R^{10}$ are each independently hydrogen or unsubstituted alkyl.

In some embodiments, $R^7$, $R^8$, $R^9$, and $R^{10}$ are each independently hydrogen or $C_{1-20}$ substituted or unsubstituted alkyl. In some embodiments, $R^7$, $R^8$, $R^9$, and $R^{10}$ are each independently hydrogen or $C_{1-10}$ substituted or unsubstituted alkyl. In some embodiments, $R^7$, $R^8$, $R^9$, and $R^{10}$ are each independently hydrogen or $C_{1-5}$ substituted or unsubstituted alkyl.

In some embodiments, the glutarate compound of Formula I has the following Formula II:

(II)

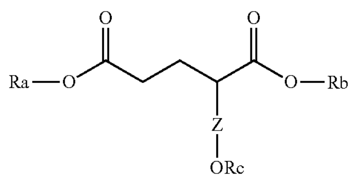

wherein

Ra and Rb are each independently a negative charge, hydrogen, Na, a straight or branched $C_1$-$C_{10}$ alkyl, or a straight or branched $C_1$-$C_{10}$ alkenyl, and Rc is optionally present, and if present, Rc is hydrogen, a straight or branched $C_1$-$C_{10}$ alkyl, or a straight or branched $C_1$-$C_{10}$ alkenyl, and if absent, Z is a double bond, and pharmaceutically acceptable solvates, salts, prodrugs, and metabolites thereof.

In some embodiments, Ra and Rb are each independently a negative charge, hydrogen, Na, a straight or branched $C_1$-$C_5$ alkyl, or a straight or branched $C_1$-$C_5$ alkenyl.

In some embodiments, if present, Rc is hydrogen, a straight or branched $C_1$-$C_5$ alkyl, or a straight or branched $C_1$-$C_5$ alkenyl.

In some embodiments, the glutarate compound is:

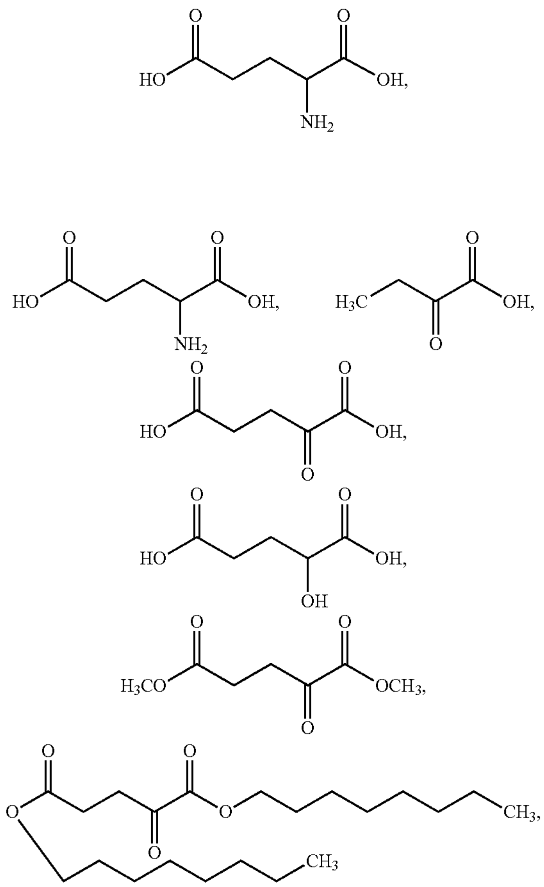

or a salt thereof. In some embodiments, the glutarate compound is:

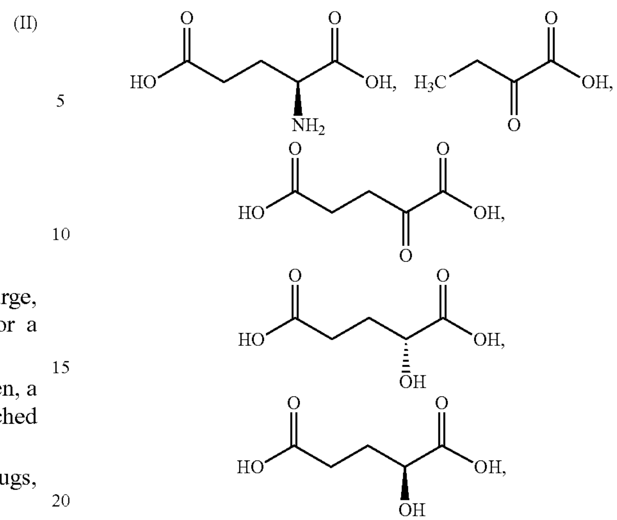

or a salt thereof.

As used herein, an "α-KG compound" refers to α-ketoglutarate (α-KG), derivatives of α-ketoglutarate (e.g., the derivatives set forth in MacKenzie, et al. (2007) Mol Cell Biol 27(9):3282-3289)), analogues of α-ketoglutarate (e.g., phosphonate analogues (e.g., those recited in Bunik, et al. (2005) Biochemistry 44(31):10552-61), esters of α-ketoglutarate (e.g., dimethyl α-ketoglutarate and octyl α-ketoglutarate), and various species specific analogues, e.g., human α-ketoglutarate, porcine α-ketoglutarate, murine α-ketoglutarate, bovine α-ketoglutarate, and the like. In some embodiments, the α-KG compound is α-ketoglutaric acid. In some embodiments, the α-KG compound is dimethyl α-ketoglutarate. In some embodiments, the α-KG compound is octyl α-ketoglutarate. As used herein, "α-ketoglutarate" and "α-ketoglutaric acid" are used interchangeably. As used herein, the abbreviation "KG" may be used to refer to the term "ketoglutarate", e.g., α-ketoglutarate is abbreviated as α-KG.

As used herein, a "2-HG compound" refers to 2-hydroxyglutaric acid, 2-hydroxypentanedioate, and compounds having 2-hydroxypentanedioate as part of its backbone structure and includes 1-alkyl-(S)-2-hydroxypentanedioate, 1-alkyl-(R)-2-hydroxypentanedioate, 1-alkenyl-(S)-2-hydroxypentanedioate, 1-alkenyl-(R)-2-hydroxypentanedioate, 5-alkyl-(S)-2-hydroxypentanedioate, 5-alkyl-(R)-2-hydroxypentanedioate, 5-alkenyl-(S)-2-hydroxypentanedioate, and 5-alkenyl-(R)-2-hydroxypentanedioate, wherein alkyl is a straight or branched $C_1$-$C_{10}$ alkyl and alkenyl is a straight or branched $C_1$-$C_{10}$ alkenyl. In some embodiments, the 2-HG compound is 1-octyl-(S)-2-hydroxypentanedioate, 1-octyl-(R)-2-hydroxypentanedioate, 5-octyl-(S)-2-hydroxypentanedioate, or 5-octyl-(R)-2-hydroxypentanedioate. In some embodiments, the 2-HG compound is disodium (S)-2-hydroxyglutarate or (S)-2-hydroxyglutaric acid (S-2HG). In some embodiments, the 2-HG compound is L-α-hydroxyglutaric acid disodium salt. As used herein, the abbreviation "HG" may be used to refer to the term "hydroxypentanedioate", e.g., 2-hydroxypentanedioate is abbreviated as 2-HG. As used herein, "2-hydroxyglutarate" and "2-hydroxyglutaric acid" are used interchangeably. In some embodiments, a 2-HG compound is S-2HG.

A "pharmaceutically acceptable solvate" refers to a solvate form of a specified compound that retains the biological effectiveness of the specified compound. Examples of solvates include compounds of the invention in combination with water, isopropanol, ethanol, methanol, dimethyl sulfoxide, ethyl acetate, acetic acid, ethanolamine, or acetone. Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of compounds of glutarate compounds are within the scope of the invention. It will also be appreciated by those skilled in organic chemistry that many organic compounds can exist in more than one crystalline form. For example, crystalline form may vary from solvate to solvate. Thus, all crystalline forms of the glutarate compounds or the pharmaceutically acceptable solvates thereof are within the scope of the present invention.

The term "pharmaceutically acceptable salt" refers to a salt form that is pharmacologically acceptable and substantially non-toxic to the subject being treated with the compound of the invention. pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

A "pharmaceutically acceptable prodrug" is a compound that may be converted under physiological conditions or by solvolysis to the specified compound or to a pharmaceutically acceptable salt of such compound. A "pharmaceutically active metabolite" refers to a pharmacologically active product produced through metabolism in the body of a specified compound or salt thereof. Prodrugs and active metabolites of a compound may be identified using routine techniques known in the art. See, e.g., Bertolini, G. et al., (1997) J. Med. Chem. 40:2011-2016; Shan, D. et al., J. Pharm. Sci., 86(7):765-767; Bagshawe K., (1995) Drug Dev. Res. 34:220-230; Bodor, N., (1984) Advances in Drug Res. 13:224-331; Bundgaard, H., Design of Prodrugs (Elsevier Press, 1985) and Larsen, I. K., Design and Application of Prodrugs, Drug Design and Development (Krogsgaard-Larsen et al., eds., Harwood Academic Publishers, 1991).

Compositions of the present invention, including pharmaceutical compositions, may include one glutarate compound or two or more different glutarate compounds, e.g., an α-KG compound and a 2-HG compound. As used herein, the terms "pharmaceutical composition" and "pharmaceutical formulation" are used interchangeably to refer to a composition suitable for pharmaceutical use in a subject. A pharmaceutical composition generally comprises an effective amount of an active agent, e.g., a glutarate compound and a pharmaceutically acceptable carrier, e.g., a buffer, adjuvant, diluent, and the like. In some embodiments, the compositions, including pharmaceutical compositions comprise a concentrated amount of at least one glutarate compound, wherein the concentrated amount is a concentration that is higher than naturally occurring concentrations of the at least one glutarate compound or its naturally occurring counterpart as found in nature.

As used herein, "pharmaceutically acceptable vehicle" and "pharmaceutically acceptable carrier" are used interchangeably and refer to and include any and all solvents, dispersion media, coatings, antibacterial and antifungal agents, isotonic and absorption delaying agents, excipients, and the like, that are compatible with pharmaceutical administration and comply with applicable standards and regulations, e.g., the pharmacopeial standards set forth in the United States Pharmacopeia and the National Formulary (USP-NF) book, for pharmaceutical administration. Thus, for example, unsterile water is excluded as a pharmaceutically acceptable carrier for, at least, intravenous administration. pharmaceutically acceptable vehicles include those known in the art. See, e.g., Remington: The Science and Practice of Pharmacy. 20$^{th}$ ed. (2000) Lippincott Williams & Wilkins. Baltimore, Md., which is herein incorporated by reference.

One or more glutarate compounds according to the present invention may be administered, preferably in the form of pharmaceutical compositions, to a subject. Preferably the subject is mammalian, more preferably, the subject is human. Preferred pharmaceutical compositions are those comprising at least one glutarate compound in a therapeutically effective amount, and a pharmaceutically acceptable vehicle.

In some embodiments, the amount of the one or more glutarate compounds administered to the subject is a therapeutically effective amount or an effective amount. As used herein, an "effective amount" is a dose that results in an observable difference as compared to a placebo. A "therapeutically effective amount", refers to an amount of one or more compounds of the present invention that, when administered to a subject, (i) treats or inhibits the particular disease, condition, or disorder, (ii) attenuates, ameliorates, or eliminates one or more symptoms of the particular disease, condition, or disorder, and/or (iii) inhibits or delays the onset of one or more symptoms of the particular disease, condition, or disorder, as compared to a control. A therapeutically effective amount of one or more compounds of the present invention will vary depending upon factors such as the given compound(s), the pharmaceutical formulation, route of administration, the type of disease or disorder, the degree of the disease or disorder, and the identity of the subject being treated, but can nevertheless be readily determined by one skilled in the art. For example, a "therapeutically effective amount" of a glutarate compound is one that inhibits or reduces the amount of an IR injury as compared to a negative control.

In some embodiments, one or more glutarate compounds are administered prior to, during, and/or after an event that causes an IR injury or a period of ischemia and/or reperfusion. In some embodiments, a therapeutically effective amount one or more glutarate compounds is administered prior to, during, and/or after the event or the period of ischemia and/or reperfusion. In some embodiments, the event is myocardial infarction, stroke, surgeries in which blood flow to a tissue is prevented, inhibited, or reduced (such as in organ transplantations), and the like. In some embodiments, the event is myocardial infarction. In some embodiments, the administration is immediately prior to the event or the period of ischemia and/or reperfusion. In some embodiments, the administration is up to 2 hours, preferably up to 1 hour, after the event or the period of ischemia and/or reperfusion. In some embodiments, the administration is within 30 minutes of the event or the period of ischemia and/or reperfusion. In some embodiments, the administration is within 1 to 2 hours of the event. In some embodiments, the administration is within 1 hour of the event. In some embodiments, the administration is within 30 minutes, 25 minutes, 20 minutes, 15 minutes, 10 minutes, or 5 minutes of the event. In some embodiments, the administration is within 30 minutes of the event. In some embodiments, the administration is within 25 minutes of the event. In some embodiments, the administration is within 20 minutes of the event. In some embodiments, the administration is within 15 minutes of the event. In some embodiments, the administration is within 10 minutes of the event. In some embodiments, the administration is within 5 minutes of the event. In some embodiments, the administration is within 1 minute of the event. In some embodiments, the administration is immediately after the occurrence of the event.

In some embodiments, a therapeutically effective amount of the one or more glutarate compounds are administered as a single dose of about 5-20, about 10-15, or about 11-12 milligrams per kilogram weight of the subject prior to, during, or after the event that causes an IR injury. In some embodiments, a therapeutically effective amount of at least one α-KG compound, such as α-KG, is administered as a single dose of about 5-15, about 10-15, or about 11-12 milligrams per kilogram weight of the subject prior to, during, or after the event that causes an IR injury. In some embodiments, the at least one glutarate compound is α-KG and the therapeutically effective amount is about 11.5 milligrams per kilogram weight of the subject. In some embodiments, a therapeutically effective amount of at least one 2-HG compound, such as S-2HG, is administered as a single dose of about 10-20, about 15-20, or about 15-16 milligrams per kilogram weight of the subject prior to, during, or after the event that causes an IR injury. In some embodiments, the at least one glutarate compound is S-2HG and the therapeutically effective amount is about 15.5 milligrams per kilogram weight of the subject. In some embodiments, the therapeutically effective amount is about 5-50 mg/kg, 5-40 mg/kg, 5-30 mg/kg, 5-20 mg/kg, 5-10 mg/kg, 10-40 mg/kg, 10-30 mg/kg, 10-20 mg/kg, or about 10-15 mg/kg of the subject. In some embodiments, the therapeutically effective amount is about 5-20 mg/kg, or about 10-15 mg/kg of the subject. In some embodiments, the therapeutically effective amount is about 5-50 mg/kg. In some embodiments, the therapeutically effective amount is about 5-40 mg/kg. In some embodiments, the therapeutically effective amount is about 5-30 mg/kg. In some embodiments, the therapeutically effective amount is about 5-20 mg/kg. In some embodiments, the therapeutically effective amount is about 5-10 mg/kg. In some embodiments, the therapeutically effective amount is about 10-40 mg/kg. In some embodiments, the therapeutically effective amount is about 10-30 mg/kg. In some embodiments, the therapeutically effective amount is about 10-20 mg/kg. In some embodiments, the therapeutically effective amount is about 10-15 mg/kg. In some embodiments, the timing of administration of the therapeutically effective amount of one or more glutarate compounds is in accordance with paragraph [0051]. The skilled artisan will appreciate that certain factors may influence the dosage required to effectively treat a subject, including but not limited to the severity of the disease or disorder, previous treatments, the general health and/or age of the subject, and other diseases present.

The one or more glutarate compounds to be administered to a subject may be provided as a pharmaceutical formulation. pharmaceutical formulations may be prepared in a unit-dosage form appropriate for the desired mode of administration. The pharmaceutical formulations of the present invention may be administered by any suitable route including oral, rectal, nasal, topical (including buccal and sublingual), vaginal, and parenteral (including subcutaneous, intramuscular, intravenous, and intradermal). It will be appreciated that the route of administration may vary with the condition and age of the recipient, the nature of the condition to be treated, and the given compound(s) of the present invention. In some embodiments, the route of administration is oral. In some embodiments, the pharmaceutical composition is formulated for parenteral administration. In some embodiments, the pharmaceutical composition is formulated for subcutaneous administration. In some embodiments, the pharmaceutical composition is formulated for intramuscular administration. In some embodiments, the pharmaceutical composition is formulated for intravenous administration. In some embodiments, the pharmaceutical composition is formulated for intraarterial administration. In some embodiments, the pharmaceutical composition is formulated for intradermal administration.

It will be appreciated that the actual dosages of the glutarate compounds used in the pharmaceutical formulations will vary according to the particular compound(s) being used, the particular composition formulated, the mode of administration, and the particular site, subject, and disease being treated. Optimal dosages for a given set of conditions may be ascertained by those skilled in the art using dosage determination tests in view of the experimental data for a given compound. Administration of prodrugs may be dosed at weight levels that are chemically equivalent to the weight levels of the fully active forms.

In some embodiments, a therapeutically effective amount of one or more glutarate compounds is administered as a daily dose of about 0.01-2, about 0.25-2, about 0.5-2, about 1-2, or about 2 grams per kilogram weight of the subject per day. In some embodiments, a therapeutically effective amount of one or more glutarate compounds is administered as a daily dose of about 0.1-1, about 0.25-1, about 0.5-1, or about 1 gram per kilogram weight of the subject per day. In some embodiments, one or more glutarate compounds is administered as a daily dose of about 0.01-1.0, about 0.01-0.5, or about 0.1-0.2 grams per kilogram weight of the subject per day. The skilled artisan will appreciate that certain factors may influence the dosage required to effectively treat a subject, including but not limited to the severity of the disease or disorder, previous treatments, the general health and/or age of the subject, and other diseases present.

The therapeutically effective amount may be administered as a single dose or as multiple doses (e.g., 2, 3, 4, 5, 6, 7, 8, 9, 10, or more doses) over a period of time. For example, a subject may be treated with one or more glutarate compounds at least once. Alternatively, the subject may be treated with one or more compounds of glutarate compounds from about one time per week to about once daily for a given treatment period. The length of the treatment period will depend on a variety of factors such as the severity of the disease or disorder, the concentration and activity of the one or more compounds of the present invention, or a combination thereof. It will also be appreciated that the effective dosage of the one or more glutarate compounds may increase or decrease over the course of a particular treatment.

In some embodiments, one or more glutarate compounds are administered to a subject in combination with an additional therapeutic agent. In some embodiments, the additional therapeutic agent is oligomycin. In some embodiments, the additional therapeutic agent is aspirin.

Toxicity and therapeutic efficacy of the one or more glutarate compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds exhibiting large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

In some embodiments, the present invention is directed to kits which comprise one or more glutarate compounds, optionally in a composition or in combination with one or more additional therapeutic agents, packaged together with one or more reagents or drug delivery devices for preventing, inhibiting, reducing, or treating an IR injury. Such kits include a carrier, package, or container that may be compartmentalized to receive one or more containers, such as vials, tubes, and the like. In some embodiments, the kits optionally include an identifying description or label or instructions relating to its use. In some embodiments, the kits comprise the one or more glutarate compounds, optionally in one or more unit dosage forms, packaged together as a pack and/or in drug delivery device, e.g., a pre-filled syringe. In some embodiments, the kits include information prescribed by a governmental agency that regulates the manufacture, use, or sale of compounds and compositions according to the present invention.

Additional Exemplary Methods of Use

The present invention provides a method of treating or reducing an ischemia-reperfusion injury (IR injury) or a method of preventing or inhibiting an ischemia-reperfusion injury (IR injury) in a subject in need thereof, comprising administering to the subject a pharmaceutical composition comprising a therapeutically effective amount of a compound of Formula I:

(I)

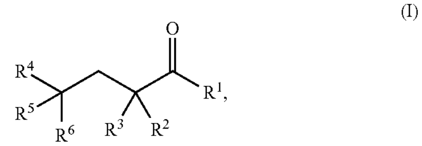

wherein: $R^1$ is hydrogen, halogen, —CHO, —$OR^7$, —$NR^8R^9$, —$COOR^7$, —$CONR^8R^9$, —$SR^{10}$, substituted or unsubstituted alkyl, or substituted or unsubstituted heteroalkyl; $R^2$ and $R^3$ are each independently hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl; or $R^2$ and $R^3$, together with the atom to which they are bound, form an oxo; $R^4$, $R^5$, and $R^6$ are each independently hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl; and $R^7$, $R^8$, $R^9$, and $R^{10}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a salt thereof; wherein the pharmaceutical composition is administered to the subject to treat, reduce, prevent, or inhibit IR injury to a tissue in the subject. A pharmaceutical composition described herein may further comprise an excipient.

In some embodiments of a compound of Formula I, $R^1$ is hydrogen, halogen, —CHO, —$OR^7$, —$NR^8R^9$, —$COOR^7$, —$CONR^8R^9$, or —$SR^{10}$. In some embodiments, $R^1$ is hydrogen, —CHO, or —$OR^7$. In some embodiments, $R^1$ is —$OR^7$, wherein $R^7$ is hydrogen, substituted or unsubstituted alkyl, or substituted or unsubstituted aryl. In some embodiments, $R^1$ is —$OR^7$, wherein $R^7$ is $C_{1-20}$ substituted or unsubstituted alkyl.

In some embodiments of a compound of Formula I, $R^2$ is hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl and $R^3$ is hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl. In some embodiments, $R^2$ is hydrogen, halogen, —CN, —CHO, or —$NR^8R^9$, wherein $R^8$ and $R^9$ are each independently hydrogen or substituted or unsubstituted alkyl. In some embodiments, $R^3$ is hydrogen, halogen, —CN, —CHO, or —$NR^8R^9$, wherein $R^8$ and $R^9$ are each independently hydrogen or substituted or unsubstituted alkyl. In some embodiments, $R^2$ and $R^3$, together with the atom to which they are bound, form an oxo.

In some embodiments of a compound of Formula I, $R^4$ is hydrogen, —CHO, —$OR^7$, —$NR^8R^9$, —$COOR^7$, or —$CONR^8R^9$. In some embodiments, $R^5$ is hydrogen, —CHO, —$OR^7$, —$NR^8R^9$, —$COOR^7$, or —$CONR^8R^9$. In some embodiments, $R^6$ is hydrogen, —CHO, —$OR^7$, —$NR^8R^9$, —$COOR^7$, or —$CONR^8R^9$.

In some embodiments of a compound of Formula I, $R^7$ is hydrogen or $C_{1-20}$ substituted or unsubstituted alkyl. In some embodiments, $R^8$ is hydrogen or $C_{1-20}$ substituted or unsubstituted alkyl. In some embodiments, $R^9$ is hydrogen or $C_{1-20}$ substituted or unsubstituted alkyl.

In some embodiments, the present invention provides a method of treating or reducing an ischemia-reperfusion injury (IR injury) or a method of preventing or inhibiting an ischemia-reperfusion injury (IR injury) in a subject in need thereof, comprising administering to the subject a pharmaceutical composition comprising a therapeutically effective amount of a compound of Formula I:

(I)

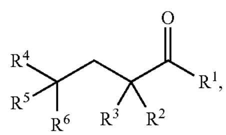

wherein: $R^1$ is —CHO, —$OR^7$, —$NR^8R^9$, —$COOR^7$, —$CONR^8R^9$, —$SR^{10}$, $R^2$ and $R^3$ are each independently hydrogen, halogen, —CN, —CHO, —$OR^7$, —$NR^8R^9$, —$Sr^{10}$, or substituted or unsubstituted alkyl; or $R^2$ and $R^3$, together with the atom to which they are bound, form an oxo; $R^4$, $R^5$, and $R^6$ are each independently hydrogen, halogen, —$OR^7$, —$NR^8R^9$, —$COOR^7$, —$CONR^8R^9$, or substituted or unsubstituted alkyl; and $R^7$, $R^8$, $R^9$, and $R^{10}$ are each independently hydrogen, substituted or unsubstituted alkyl, or substituted or unsubstituted heteroalkyl; or a salt thereof.

In some embodiments, the present invention provides a method of treating or reducing an ischemia-reperfusion injury (IR injury) or a method of preventing or inhibiting an ischemia-reperfusion injury (IR injury) in a subject in need thereof, comprising administering to the subject a pharmaceutical composition comprising a therapeutically effective amount of a compound of Formula I:

(I)

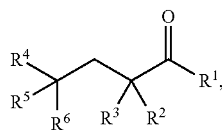

wherein: $R^1$ is —$OR^7$ or —$NR^8R^9$; $R^2$ and $R^3$ are each independently hydrogen, —CHO, —$OR^7$, —$NR^8R^9$, or unsubstituted alkyl; or $R^2$ and $R^3$, together with the atom to which they are bound, form an oxo; $R^4$, $R^5$, and $R^6$ are each independently hydrogen, —$OR^7$, —$NR^8R^9$, or unsubstituted alkyl; and $R^7$, $R^8$, $R^9$, and $R^{10}$ are each independently hydrogen, or substituted or unsubstituted alkyl; or a salt thereof.

In some embodiments, the present invention provides a method of treating or reducing an ischemia-reperfusion injury (IR injury) or a method of preventing or inhibiting an ischemia-reperfusion injury (IR injury) in a subject in need thereof, comprising administering to the subject a pharmaceutical composition comprising a therapeutically effective amount of a compound of Formula I:

(I)

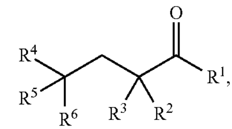

wherein: $R^1$ is —$OR^7$; $R^2$ and $R^3$, together with the atom to which they are bound, form an oxo; $R^4$, $R^5$, and $R^6$ are each independently hydrogen or unsubstituted alkyl; and $R^7$, $R^8$, $R^9$, and $R^{10}$ are each independently hydrogen or unsubstituted alkyl; or a salt thereof.

The present invention provides a method of treating or reducing an ischemia-reperfusion injury (IR injury) to a tissue in a subject, comprising administering to the subject a therapeutically effective amount of a pharmaceutical composition comprising: a therapeutically effective amount of a compound of Formula III:

(III)

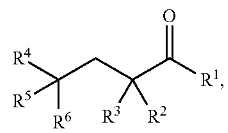

wherein: $R^1$ is hydrogen, halogen, —CHO, —$OR^7$, —$NR^8R^9$, —$COOR^7$, —$CONR^8R^9$, —$SR^{10}$, substituted or unsubstituted alkyl, or substituted or unsubstituted heteroalkyl; $R^2$ and $R^3$ are each independently hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl; or $R^2$ and $R^3$, together with the atom to which they are bound, form an oxo; $R^4$ and $R^5$ are each independently hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl; $R^6$ is halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl; and $R^7$, $R^8$, $R^9$, and $R^{10}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a salt thereof; wherein the pharmaceutical composition is administered to the subject to treat or reduce IR injury to a tissue in the subject.

In some embodiments of a compound of Formula III, $R^1$ is hydrogen, halogen, —CHO, —$OR^7$, —$NR^8R^9$, —$COOR^7$, —$CONR^8R^9$, or —$SR^{10}$. In some embodiments, $R^1$ is hydrogen, —CHO, or —$OR^7$. In some embodiments, $R^1$ is —$OR^7$, wherein $R^7$ is hydrogen, substituted or unsubstituted alkyl, or substituted or unsubstituted aryl. In some embodiments, $R^1$ is —$OR^7$, wherein $R^7$ is $C_{1-20}$ substituted or unsubstituted alkyl.

In some embodiments of a compound of Formula III, $R^2$ is hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl and $R^3$ is hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl. In some embodiments, $R^2$ is hydrogen, halogen, —CN, —CHO, or —$NR^8R^9$, wherein $R^8$ and $R^9$ are each independently hydrogen or substituted or unsubstituted alkyl. In some embodiments, $R^3$ is hydrogen, halogen, —CN, —CHO, or —$NR^8R^9$, wherein $R^8$ and $R^9$ are each independently hydrogen or substituted or unsubstituted alkyl. In some embodiments, $R^2$ and $R^3$, together with the atom to which they are bound, form an oxo.

In some embodiments of a compound of Formula III, $R^4$ is hydrogen, —CHO, —$OR^7$, —$NR^8R^9$, —$COOR^7$, or —$CONR^8R^9$. In some embodiments, $R^5$ is hydrogen, —CHO, —$OR^7$, —$NR^8R^9$, —$COOR^7$, or —$CONR^8R^9$. In some embodiments, $R^6$ is —CHO, —$OR^7$, —$NR^8R^9$, —$COOR^7$, or —$CONR^8R^9$.

In some embodiments of a compound of Formula III, $R^7$ is hydrogen or $C_{1-20}$ substituted or unsubstituted alkyl. In some embodiments, $R^8$ is hydrogen or $C_{1-20}$ substituted or unsubstituted alkyl. In some embodiments, $R^9$ is hydrogen or $C_{1-20}$ substituted or unsubstituted alkyl.

In some embodiments, the present invention provides a method of treating or reducing an ischemia-reperfusion injury (IR injury) or a method of preventing or inhibiting an ischemia-reperfusion injury (IR injury) in a subject in need thereof, comprising administering to the subject a pharmaceutical composition comprising a therapeutically effective amount of a compound of Formula III:

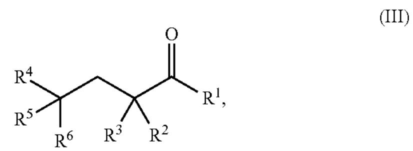

wherein: $R^1$ is —CHO, —$OR^7$, —$NR^8R^9$, —$COOR^7$, —$CONR^8R^9$, —$SR^{10}$, $R^2$ and $R^3$ are each independently hydrogen, halogen, —CN, —CHO, —$OR^7$, —$NR^8R^9$, —$SR^{10}$, or substituted or unsubstituted alkyl; or $R^2$ and $R^3$, together with the atom to which they are bound, form an oxo; $R^4$ and $R^5$ are each independently hydrogen, halogen, —$OR^7$, —$NR^8R^9$, —$COOR^7$, —$CONR^8R^9$, or substituted or unsubstituted alkyl; $R^6$ is halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl; and $R^7$, $R^8$, $R^9$, and $R^{10}$ are each independently hydrogen, substituted or unsubstituted alkyl, or substituted or unsubstituted heteroalkyl; or a salt thereof.

In some embodiments, the present invention provides a method of treating or reducing an ischemia-reperfusion injury (IR injury) or a method of preventing or inhibiting an ischemia-reperfusion injury (IR injury) in a subject in need thereof, comprising administering to the subject a pharmaceutical composition comprising a therapeutically effective amount of a compound of Formula III:

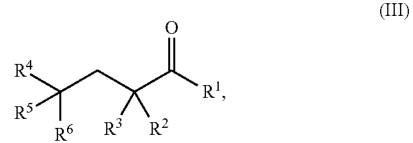

wherein: $R^1$ is —$OR^7$ or —$NR^8R^9$; $R^2$ and $R^3$ are each independently hydrogen, —CHO, —$OR^7$, —$NR^8R^9$, or unsubstituted alkyl; or $R^2$ and $R^3$, together with the atom to which they are bound, form an oxo; $R^4$ and $R^5$ are each independently hydrogen, —$OR^7$, —$NR^8R^9$, or unsubstituted alkyl; $R^6$ is —$NR^8R^9$, —$COOR^7$, or —$CONR^8R^9$, and $R^7$, $R^8$, $R^9$, and $R'''$ are each independently hydrogen, or substituted or unsubstituted alkyl; or a salt thereof.

In some embodiments, the present invention provides a method of treating or reducing an ischemia-reperfusion injury (IR injury) or a method of preventing or inhibiting an ischemia-reperfusion injury (IR injury) in a subject in need thereof, comprising administering to the subject a pharmaceutical composition comprising a therapeutically effective amount of a compound of Formula III:

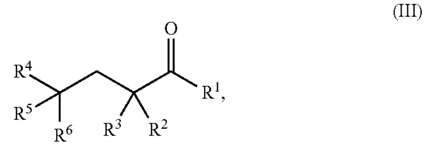

wherein: $R^1$ is —$OR^7$; $R^2$ and $R^3$, together with the atom to which they are bound, form an oxo; $R^4$ and $R^5$ are each independently hydrogen or unsubstituted alkyl; $R^6$ is —$COOR^7$, $R^7$ is hydrogen; and $R^8$, $R^9$, and $R'''$ are each independently hydrogen or unsubstituted alkyl; or a salt thereof.

In some embodiments, the present invention provides a method of treating or reducing an ischemia-reperfusion injury (IR injury) or a method of preventing or inhibiting an ischemia-reperfusion injury (IR injury) in a subject in need thereof, comprising administering to the subject a pharmaceutical composition comprising a therapeutically effective amount of a compound represented by the structure:

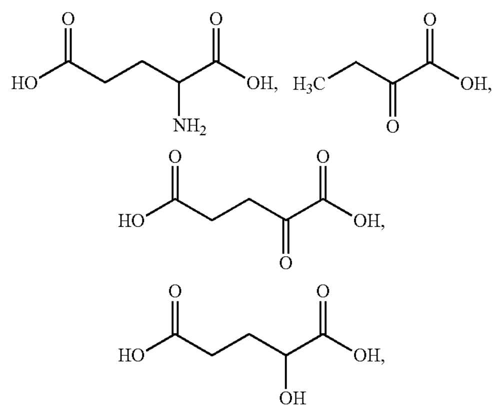

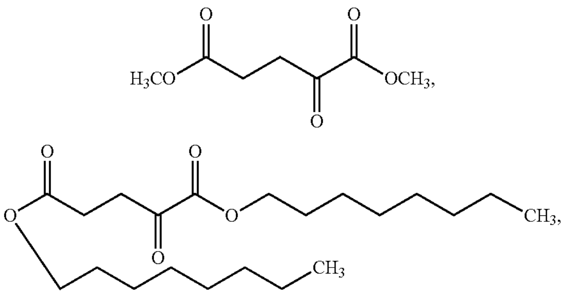

or a salt thereof.

In some embodiments, the present invention provides a method of treating or reducing an ischemia-reperfusion injury (IR injury) or a method of preventing or inhibiting an ischemia-reperfusion injury (IR injury) in a subject in need thereof, comprising administering to the subject a pharmaceutical composition comprising a therapeutically effective amount of a compound represented by the structure:

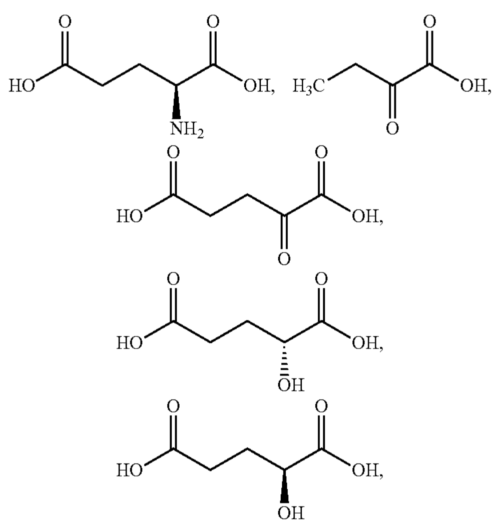

or a salt thereof.

In some embodiments, a compound of Formula I or Formula III described above is administered during an event that causes IR injury, reperfusion injury, or both. In some embodiments, the event is myocardial infarction, stroke, surgeries in which blood flow to a tissue is prevented such as in organ transplantations, and the like. In some embodiments, the event is myocardial infarction. In some embodiments, the compound of Formula I or Formula III is α-KG. In some embodiments, the compound of Formula I or Formula III is a 2-HG compound. In some embodiments, the compound of Formula I or Formula III is S-2HG.

In other embodiments, a compound of Formula I or Formula III is administered after an event that causes IR injury, reperfusion injury, or both. In some embodiments, the event is myocardial infarction, stroke, surgeries in which blood flow to a tissue is prevented such as in organ transplantations, and the like. In some embodiments, the event is myocardial infarction. In some embodiments, the compound of Formula I or Formula III is α-KG. In some embodiments, the compound of Formula I or Formula III is a 2-HG compound. In some embodiments, the compound of Formula I or Formula III is S-2HG.

In some embodiments, a compound of Formula I or Formula III is administered within 1 to 2 hours of the event. In some embodiments, the compound of Formula I or Formula III is administered within 1 hour of the event. In some embodiments, the compound of Formula I or Formula III is administered within 30 minutes, 25 minutes, 20 minutes, 15 minutes, 10 minutes, or 5 minutes of the event. In some embodiments, the compound of Formula I or Formula III is administered within 30 minutes of the event. In some embodiments, the compound of Formula I or Formula III is administered within 25 minutes of the event. In some embodiments, the compound of Formula I or Formula III is administered within 20 minutes of the event. In some embodiments, the compound of Formula I or Formula III is administered within 15 minutes of the event. In some embodiments, the compound of Formula I or Formula III is administered within 10 minutes of the event. In some embodiments, the compound of Formula I or Formula III is administered within 5 minutes of the event. In some embodiments, the compound of Formula I or Formula III is administered within 1 minute of the event. In some embodiments, the compound of Formula I or Formula III is administered immediately after the occurrence of the event. In some embodiments, the event is myocardial infarction, stroke, surgeries in which blood flow to a tissue is prevented such as in organ transplantations, and the like. In some embodiments, the event is myocardial infarction. In some embodiments, the compound of Formula I or Formula III is α-KG. In some embodiments, the compound of Formula I or Formula III is a 2-HG compound. In some embodiments, the compound of Formula I or Formula III is S-2HG.

In some embodiments, the compound of Formula I or Formula III is α-KG. In some embodiments, α-KG is administered within 1 to 2 hours of the event. In some embodiments, α-KG is administered within 1 hour of the event. In some embodiments, α-KG is administered within 30 minutes, 25 minutes, 20 minutes, 15 minutes, 10 minutes, or 5 minutes of the event. In some embodiments, α-KG is administered within 30 minutes of the event. In some embodiments, α-KG is administered within 25 minutes of the event. In some embodiments, α-KG is administered within 20 minutes of the event. In some embodiments, α-KG is administered within 15 minutes of the event. In some embodiments, α-KG is administered within 10 minutes of the event. In some embodiments, α-KG is administered within 5 minutes of the event. In some embodiments, α-KG is administered within 1 minute of the event. In some embodiments, α-KG is administered immediately after the occurance of the event. In some embodiments, the event is myocardial infarction, stroke, surgeries in which blood flow to a tissue is prevented such as in organ transplantations, and the like. In some embodiments, the event is myocardial infarction.

In some embodiments, the compound of Formula I or Formula III is a 2-HG compound. In some embodiments, a 2-HG compound is administered within 1 to 2 hours of the event. In some embodiments, the 2-HG compound is administered within 1 hour of the event. In some embodiments, the 2-HG compound is administered within 30 minutes, 25 minutes, 20 minutes, 15 minutes, 10 minutes, or 5 minutes of the event. In some embodiments, the 2-HG compound is administered within 30 minutes of the event. In some embodiments, the 2-HG compound is administered within 25 minutes of the event. In some embodiments, the 2-HG compound is administered within 20 minutes of the event. In some embodiments, the 2-HG compound is administered within 15 minutes of the event. In some embodiments, the 2-HG compound is administered within 10 minutes of the event. In some embodiments, the 2-HG compound is administered within 5 minutes of the event. In some embodiments, the 2-HG compound is administered within 1 minute of the event. In some embodiments, the 2-HG compound is administered immediately after the occurrence of the event. In some embodiments, the event is myocardial infarction, stroke, surgeries in which blood flow to a tissue is prevented such as in organ transplantations, and the like. In some embodiments, the event is myocardial infarction.

In some embodiments, the compound of Formula I or Formula III is S-2HG. In some embodiments, S-2HG is administered within 1 to 2 hours of the event. In some embodiments, S-2HG is administered within 1 hour of the event. In some embodiments, S-2HG is administered within 30 minutes, 25 minutes, 20 minutes, 15 minutes, 10 minutes, or 5 minutes of the event. In some embodiments, S-2HG is administered within 30 minutes of the event. In some embodiments, S-2HG is administered within 25 minutes of the event. In some embodiments, S-2HG is administered within 20 minutes of the event. In some embodiments, S-2HG is administered within 15 minutes of the event. In some embodiments, S-2HG is administered within 10 minutes of the event. In some embodiments, S-2HG is administered within 5 minutes of the event. In some embodiments, S-2HG is administered within 1 minute of the event. In some embodiments, S-2HG is administered immediately after the occurrence of the event. In some embodiments, the event is myocardial infarction, stroke, surgeries in which blood flow to a tissue is prevented such as in organ transplantations, and the like. In some embodiments, the event is myocardial infarction.

In some embodiments, the therapeutically effective amount is about 5-50 mg/kg, 5-40 mg/kg, 5-30 mg/kg, 5-20 mg/kg, 5-10 mg/kg, 10-40 mg/kg, 10-30 mg/kg, 10-20 mg/kg, or about 10-15 mg/kg of the subject. In some embodiments, the therapeutically effective amount is about 5-20 mg/kg, or about 10-15 mg/kg of the subject. In some embodiments, the therapeutically effective amount is about 5-50 mg/kg. In some embodiments, the therapeutically effective amount is about 5-40 mg/kg. In some embodiments, the therapeutically effective amount is about 5-30 mg/kg. In some embodiments, the therapeutically effective amount is about 5-20 mg/kg. In some embodiments, the therapeutically effective amount is about 5-10 mg/kg. In some embodiments, the therapeutically effective amount is about 10-40 mg/kg. In some embodiments, the therapeutically effective amount is about 10-30 mg/kg. In some embodiments, the therapeutically effective amount is about 10-20 mg/kg. In some embodiments, the therapeutically effective amount is about 10-15 mg/kg.

In some embodiments, the compound of Formula I or Formula III is administered as a single dose.

In some embodiments, the compound of Formula I or Formula III is administered to the subject in combination with an additional therapeutic agent. In some embodiments, the additional therapeutic agent is oligomycin. In some embodiments, the additional therapeutic agent is aspirin.

In some embodiments, in the event that a method is for preventing or inhibiting an ischemia-reperfusion injury (IR injury) to a tissue in a subject, the compound of Formula I or Formula III is administered prior to an event that causes IR injury, reperfusion injury, or both. In some embodiments, the event is myocardial infarction, stroke, surgeries in which blood flow to a tissue is prevented such as in organ transplantations, and the like. In some embodiments, the event is myocardial infarction. In some embodiments, the compound of Formula I or Formula III is α-KG. In some embodiments, the compound of Formula I or Formula III is a 2-HG compound. In some embodiments, the compound of Formula I or Formula III is S-2HG.

In some embodiments, further disclosed herein is a method of increasing cyclophilin D (CypD)-Complex V formation comprising contacting a cell with a compound of Formula III:

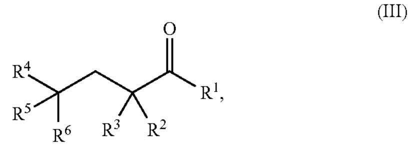

(III)

wherein: $R^1$ is hydrogen, halogen, —CHO, —$OR^7$, —$NR^8R^9$, —$COOR^7$, —$CONR^8R^9$, —$SR^{10}$, substituted or unsubstituted alkyl, or substituted or unsubstituted heteroalkyl; $R^2$ and $R^3$ are each independently hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl; or $R^2$ and $R^3$, together with the atom to which they are bound, form an oxo; and $R^5$ are each independently hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl; $R^6$ is halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl; and $R^7$, $R^8$, $R^9$, and $R^{10}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or a salt thereof. In some embodiments, $R^1$ is hydrogen, —CHO, or —$OR^7$. In some embodiments, $R^1$ is —$OR^7$, wherein $R^7$ is hydrogen, substituted or unsubstituted alkyl, or substituted or unsubstituted aryl. In some embodiments, $R^1$ is —$OR^7$, wherein $R^7$ is $C_{1-20}$ substituted or unsubstituted alkyl. In some embodiments, $R^2$ is hydrogen, halogen, —CN, —CHO, or —$NR^8R^9$, wherein $R^8$ and $R^9$ are each independently hydrogen or substituted or unsubstituted alkyl. In some embodiments, $R^2$ and $R^3$, together with the atom to which they are bound, form an oxo. In some embodiments, $R^4$ and $R^5$ are each independently hydrogen, —CHO, —$OR^7$, —$NR^8R^9$, —$COOR^7$, or —$CONR^8R^9$, wherein $R^7$, $R^8$, and $R^9$ are each independently hydrogen or $C_{1-20}$ substituted or unsubstituted alkyl. In some embodiments, $R^6$ is —CHO, —$OR^7$, —$NR^8R^9$, —$COOR^7$, or —$CONR^8R^9$, wherein $R^7$, $R^8$, and $R^9$ are each independently hydrogen or $C_{1-20}$ substituted or unsubstituted alkyl. In some embodiments, $R^6$ is —$COOR^7$ or —$CONR^8R^9$, wherein $R^7$, $R^8$, and $R^9$ are each independently hydrogen or $C_{1-20}$ substituted or unsubstituted alkyl. In some embodiments, a compound of Formula III is alpha-ketoglutaric acid (α-KG). In some embodiments, a compound of Formula III is dimethyl 2-oxoglutarate. In some embodiments, a compound of Formula III is a 2-HG compound. In some embodiments, a compound of Formula III is 2-hydroxyglutaric acid. In some embodiments, a compound of Formula III is S-2-hydroxyglutaric acid. In some embodiments, the increase in cyclophilin D-Complex V formation is relative to the formation of CypD and Complex V of an equivalent cell in the absence of a compound of Formula III. In some embodiments, the cell is from a cardiac tissue. In some embodiments, the cell is from a mammalian cardiac tissue. In some embodiments, the cell is from a human cardiac tissue.

Additional Exemplary Pharmaceutical Compositions and Formulations

The one or more glutarate compounds to be administered to a subject may be provided as a pharmaceutical composition or formulation. Pharmaceutical formulations may be prepared in a unit-dosage form appropriate for the desired mode of administration. The pharmaceutical formulations of the present disclosure may be administered by any suitable route including oral, rectal, nasal, topical (including buccal and sublingual), vaginal, and parenteral (including subcutaneous, intramuscular, intravenous, and intradermal). It will be appreciated that the route of administration may vary with the condition and age of the recipient, the nature of the condition to be treated, and the given compound(s) of the present disclosure. In some embodiments, the route of administration is oral.

In some embodiments, pharmaceutical compositions disclosed herein comprise a therapeutically effective amount of one or more compounds of the present disclosure, and a pharmaceutically acceptable carrier or diluent. As used herein the language "pharmaceutically acceptable carrier" is intended to include any and all solvents, dispersion media, coatings, antibacterial, and antifungal agents, isotonic and absorption delaying agents, stabilizers, diluents, suspending agents, thickening agents, excipients, and the like, compatible with pharmaceutical administration. The pharmaceutical carrier employed may be either a solid or liquid.

Pharmaceutical compositions are optionally manufactured in a conventional manner, such as, by way of example only, by means of conventional mixing, dissolving, granulating, dragee-making, levigating, emulsifying, encapsulating, entrapping or compression processes.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The term "pharmaceutical combination" as used herein, means a product that results from the mixing or combining of more than one active ingredient and includes both fixed and non-fixed combinations of the active ingredients. The term "fixed combination" means that the active ingredients, e.g., a compound described herein and a co-agent, are both administered to a patient simultaneously in the form of a single entity or dosage. The term "non-fixed combination" means that the active ingredients, e.g., a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

The pharmaceutical compositions described herein are formulated into any suitable dosage form, including but not limited to, aqueous oral dispersions, liquids, gels, syrups, elixirs, slurries, suspensions and the like, for oral ingestion by an individual to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, the compositions are formulated into capsules. In some embodiments, the compositions are formulated into solutions (for example, for IV administration).

The pharmaceutical solid dosage forms described herein optionally include a compound described herein and one or more pharmaceutically acceptable additives or excipients such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In still other aspects, using standard coating procedures, such as those described in Remington's Pharmaceutical Sciences, 20th Edition (2000), a film coating is provided around the compositions. In some embodiments, the compositions are formulated into particles (for example for administration by capsule) and some or all of the particles are coated. In some embodiments, the compositions are formulated into particles (for example for administration by capsule) and some or all of the particles are microencapsulated. In some embodiments, the compositions are formulated into particles (for example for administration by capsule) and some or all of the particles are not microencapsulated and are uncoated.

In some embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

Examples of a "carrier" or "carrier materials" include excipients in pharmaceutics and should be selected on the basis of compatibility with compounds disclosed herein, such as, compounds of Formula I or Formula III, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, poly sorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

A "measurable serum concentration" or "measurable plasma concentration" describes the blood serum or blood plasma concentration, typically measured in mg, or ng of therapeutic agent per mL, dL, or L of blood serum, absorbed into the bloodstream after administration. As used herein, measurable plasma concentrations are typically measured in ng/ml or μg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Steady state," as used herein, is when the amount of drug administered is equal to the amount of drug eliminated within one dosing interval resulting in a plateau or constant plasma drug exposure.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

EXAMPLES

The following examples are intended to illustrate but not to limit the invention.

Example 1

Figure 2:
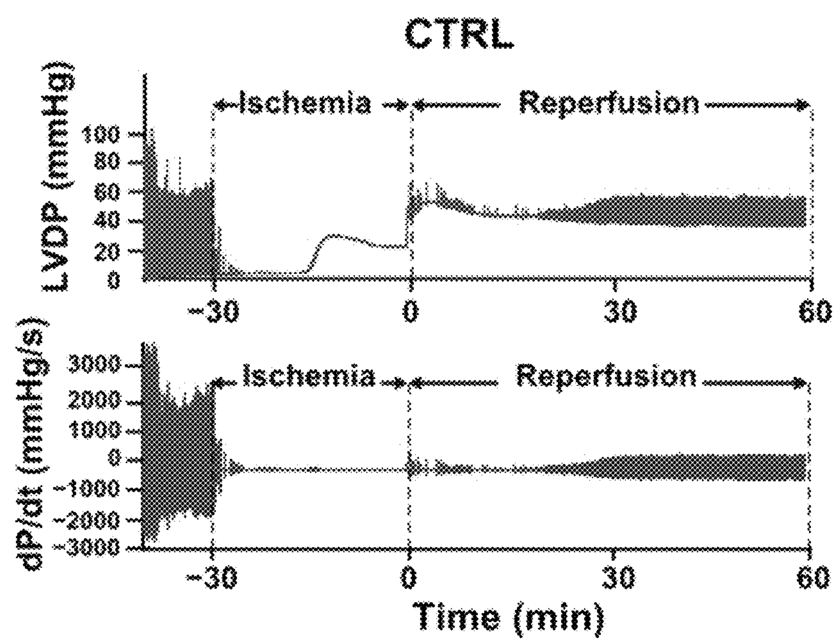
Figure 3:
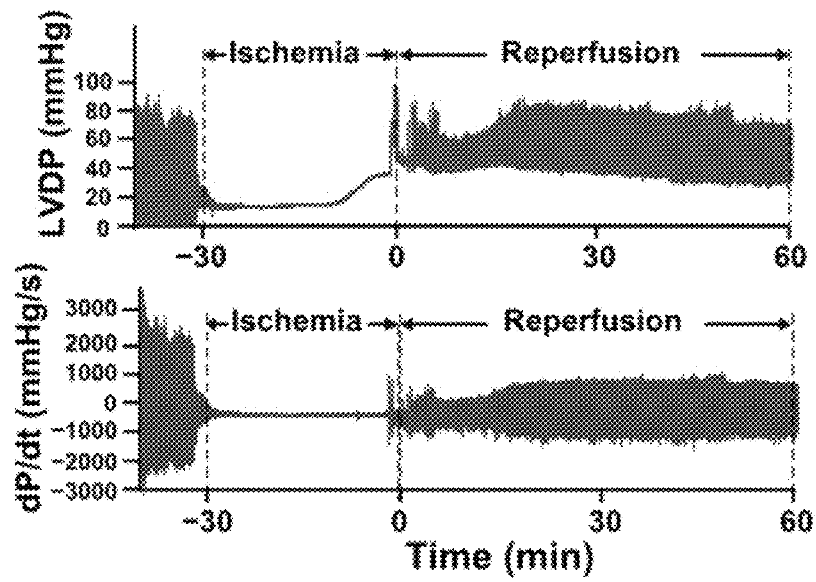
Figure 4:
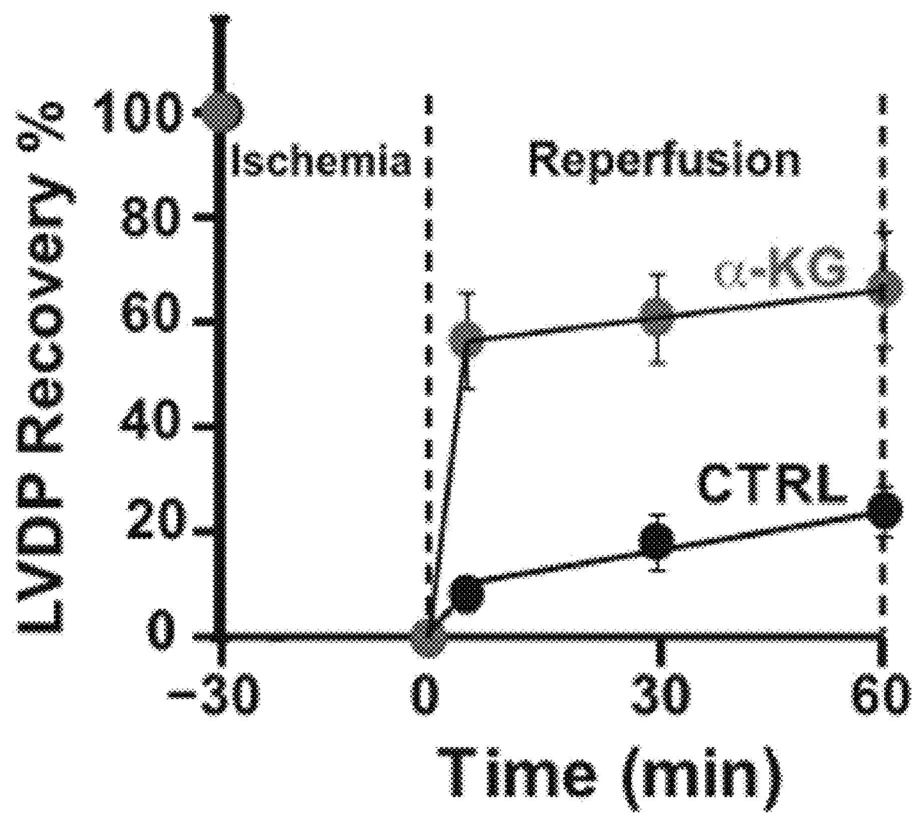
Figure 5:
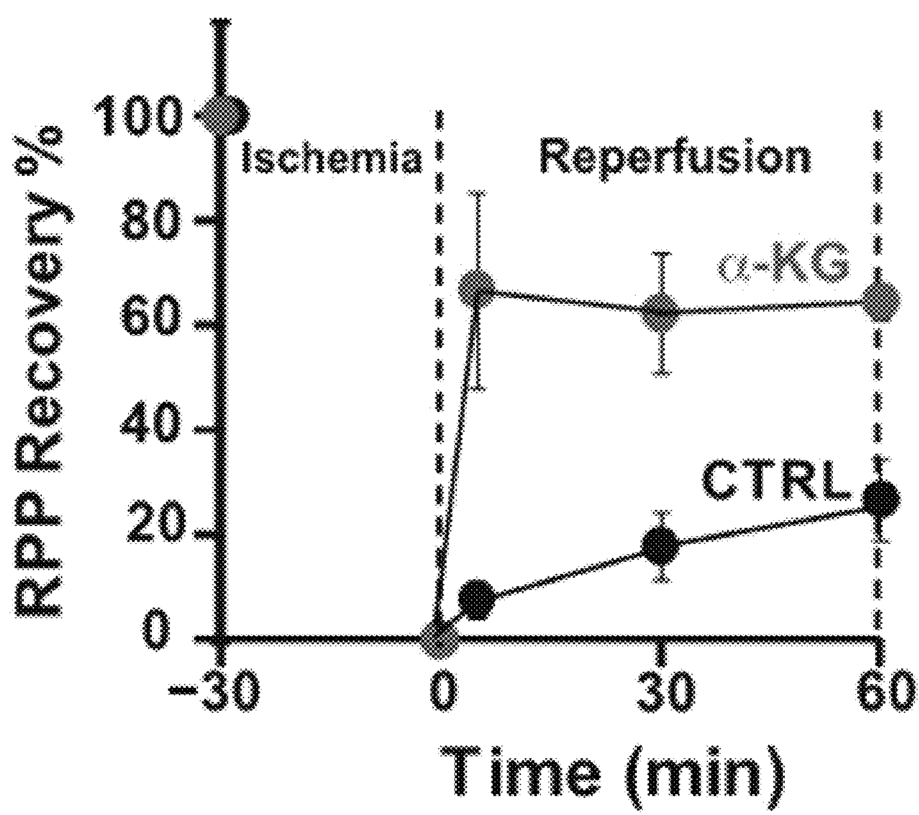
Figure 6:
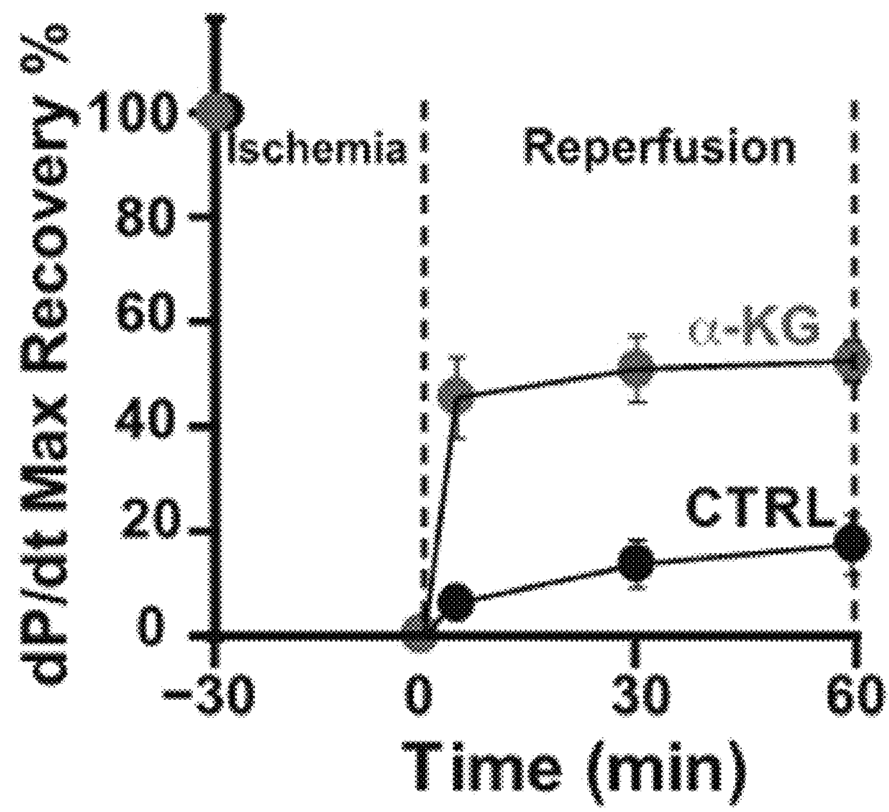

Post-Ischemic Application of α-KG Rapidly Restores Heart Hemodynamic Parameters Ex Vivo The protective effect of α-KG on heart hemodynamic parameters in ex vivo model of ischemia-reperfusion injury (IR injury) was examined. Isolated Langendorff perfused hearts were subjected to 30 minutes ischemia followed by 60 minutes reperfusion with Krebs Henseleit (KH) buffer containing 800 μM α-KG or with KH buffer as control (FIG. 1). Administration of α-KG during reperfusion rapidly restored the heart function within the first few minutes of reperfusion as the left ventricle developed pressure (LVDP) was much higher compared to control treatment (FIG. 2, FIG. 3, and FIG. 4). Rate pressure product (RPP), which is calculated as LVDPxheart rate, was also significantly higher in α-KG with about 70% recovery observed after 5 minutes of reperfusion vs. 5% in the control group, and about 80% after 30 minutes of reperfusion in α-KG compared to only 20% in control group (FIG. 5). The α-KG group also showed a much better LV $dP/dt_{max}$ compared to CTRL hearts (FIG. 6).

Because the first few minutes of reperfusion are critical in myocardial protection. These results suggest that α-KG could serve as a novel therapeutic agent for targeting the critical first few minutes of reperfusion to rapidly restore the heart function and reduce infarct size. Indeed, this was confirmed by the following in vivo experiments.

Example 2

Figure 7:
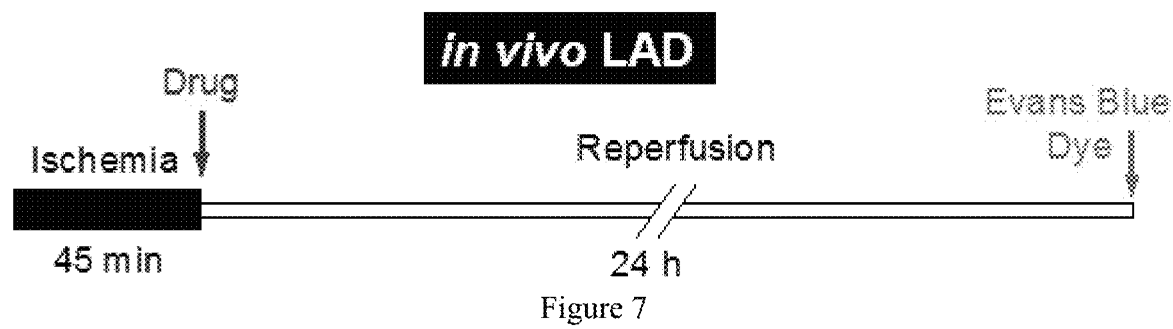
FIG. 7, FIG. 8, and FIG. 9 show that α-KG reduces myocardial infarct size in IR injury in in vivo mouse model.
Figure 8:
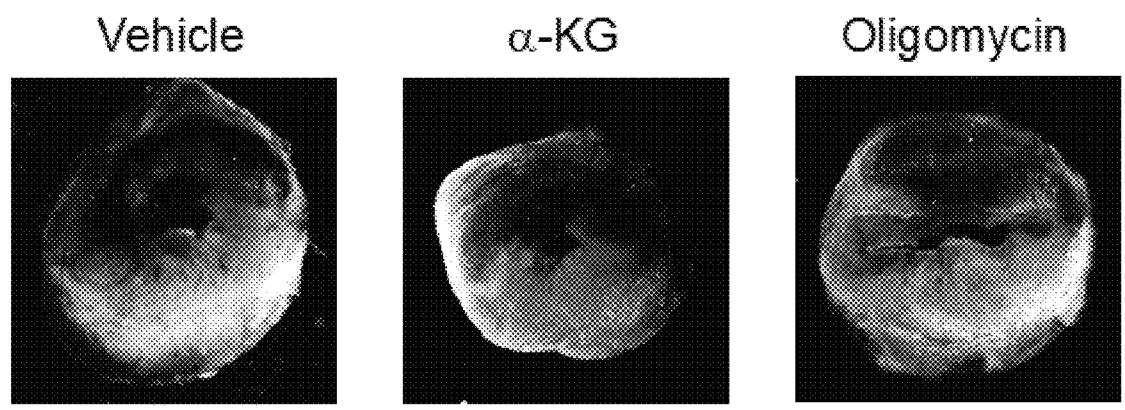
Figure 9:
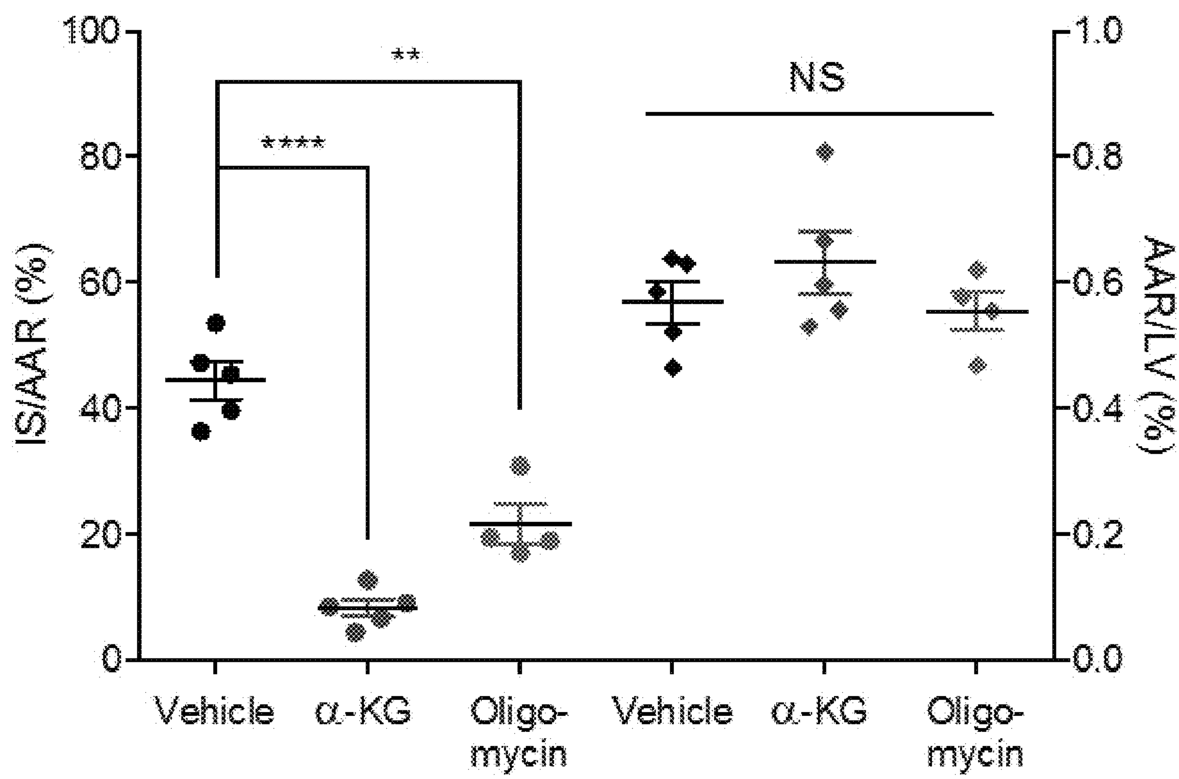

Administration of α-KG at the Onset of Reperfusion Reduces Myocardial Infarct Size In Vivo The protective role of α-KG in in vivo mouse model of IR injury, which is a close representation of the intact heart, was examined. The left coronary artery was occluded for 30 minutes followed by 24 hours of reperfusion (FIG. 7). One single bolus of α-KG (800 unoptimized) given through the tail vein at the onset of reperfusion reduced the infarct size in mice by about 70% (FIG. 8 and FIG. 9). The smaller infarct size in α-KG group was not due to smaller AAR (area at risk) since both groups were subjected to a comparable degree of ischemic risk. Further experiments show that 200 μM of α-KG confers similar levels of protection as 800 μM of α-KG. These data demonstrate a robust protective role of α-KG against IR injury in vivo.

Example 3

Role of Complex V Inhibition in Protection

Figure 10:
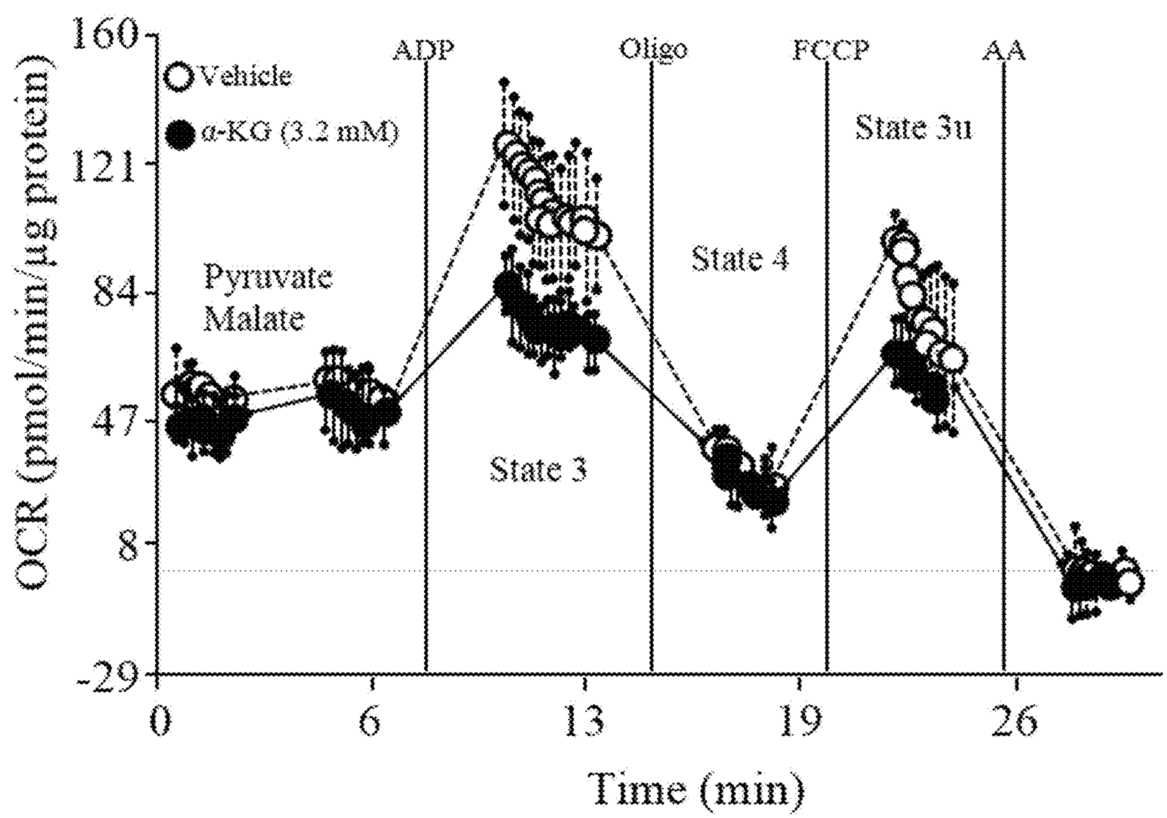
FIG. 10 and FIG. 11 show that α-KG inhibits ATP synthase in mouse heart mitochondria.
Figure 11:
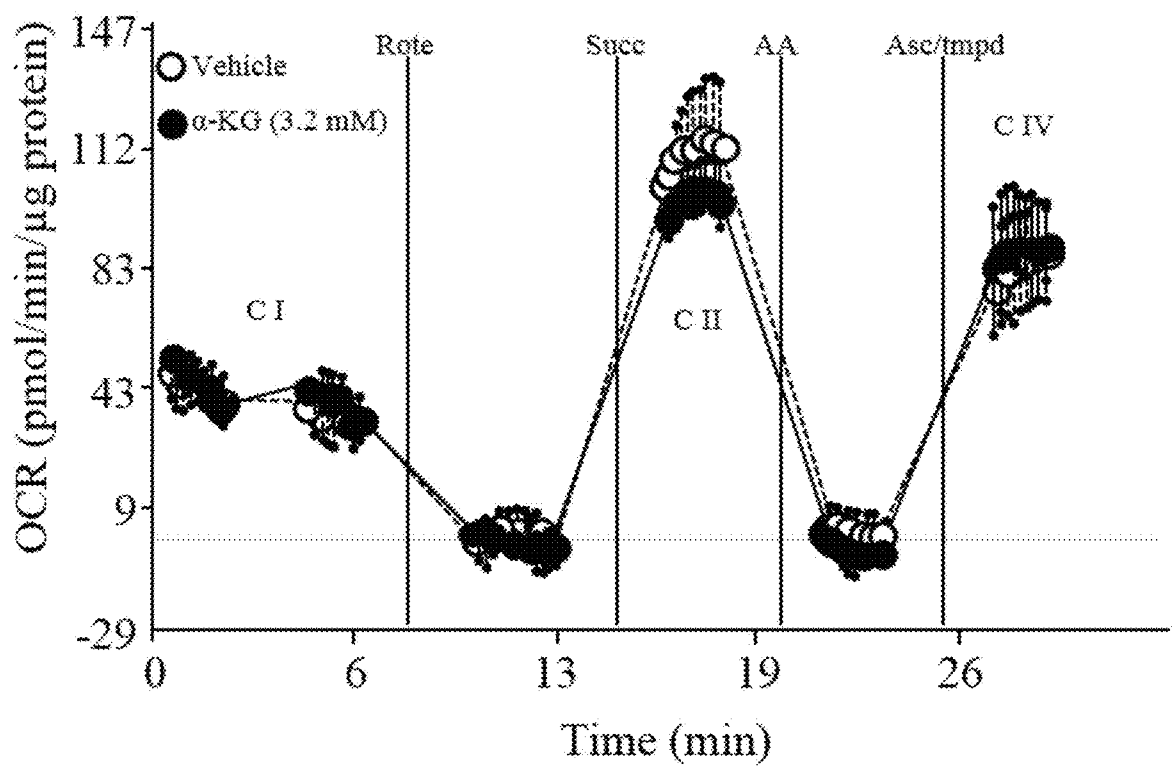

As provided in FIG. 10, α-KG inhibits complex V activity in mitochondria isolated from mouse heart at the baseline. The mitochondrial $F_1F_O$ ATP synthase is the main source of ATP in mammals. The ATP synthase can switch to an ATP hydrolase under certain conditions, including myocardial ischemia, resulting in the loss of as much as 50-90% of the total ATP. Experiments were conducted to determine whether oligomycin can alleviate IR injury when administered at the time of reperfusion. Oligomycin was found to be toxic at 5 μM, however, lower doses (e.g., 10 nM) of oligomycin given at reperfusion were found to significantly reduce myocardial infarct size in mice (FIG. 8 and FIG. 9). These results are unexpected and suggest that inhibition of ATP synthase is at least partially responsible for the protective effect of α-KG. Since oligomycin is considered unsafe for treating IR injury due to concerns of poisoning ATP production in healthy tissue and α-KG is a naturally occurring metabolite having proven safety profiles and is more effective in reducing IR injury, α-KG alone or in combination with low doses of oligomycin can be used to treat or reduce IR injury.

Example 4

Protection by α-KG is Independent of HIF, PHD, and Epigenetics

Figure 12:
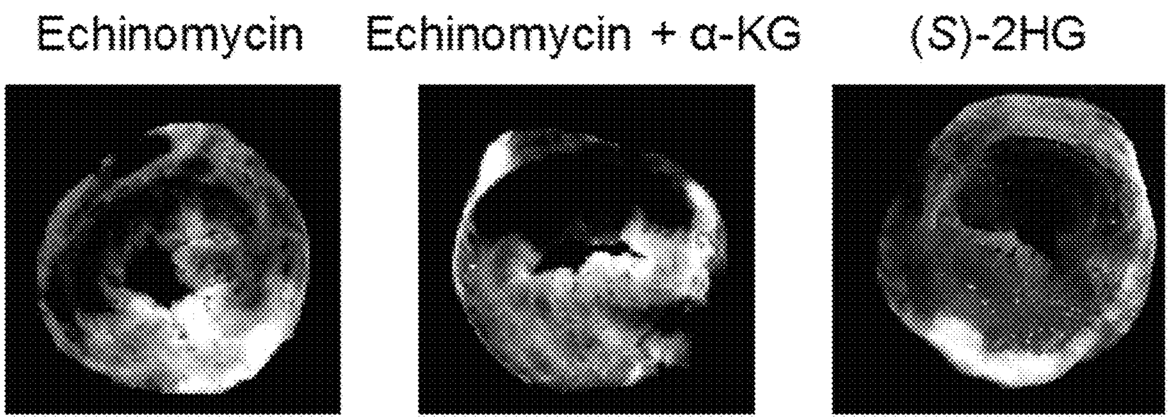
FIG. 12 are representative triphenyl tetrazolium chloride (TTC) stained cross-sections of the heart showing protection by α-KG is independent of HIF and PHD. The LAD was occluded for 45 minutes followed by 24 hours of reperfusion. One single IV bolus of echinomycin (227 nM), echinomycin (227 nM) plus α-KG (800 μM), or S-2HG (800 μM) was administered at reperfusion. Infarcted tissue is white, the rest of the area at risk is red, and non-risk tissue is dark blue.

Since HIF-1 protein stability is regulated by prolyl hydroxylase domain containing proteins (PHD; encoded by Egl nine homolog or EGLN genes) for which α-KG is a cofactor (as is oxygen), it was surprising to find that neither HIF-1 nor PHD is involved in protection by α-KG. Not only is α-KG fully protective in the presence of the HIF-1 inhibitor echinomycin, but the PHD inhibitor (S)-2-hydroxyglutarate (S-2HG) confers similar extents of protection as α-KG (FIG. 12). Therefore, α-KG and/or S-2HG can be used to treat or reduce IR injury.

In addition to PHD in hypoxic response, many other dioxygenases also use α-KG as a co-substrate in a variety of cellular processes including epigenetic regulation. Because the protective effect of α-KG manifests within minutes of injection as shown by ex vivo experiments herein, and an inhibitor of α-KG-dependent epigenetic enzymes (S-2HG) also confers similar extents of protection against IR injury in vivo, epigenetic mechanisms can largely be ruled out.

Example 5

Protection by an α-KG Metabolite, Succinyl-CoA, Against IR Injury

Figure 13:
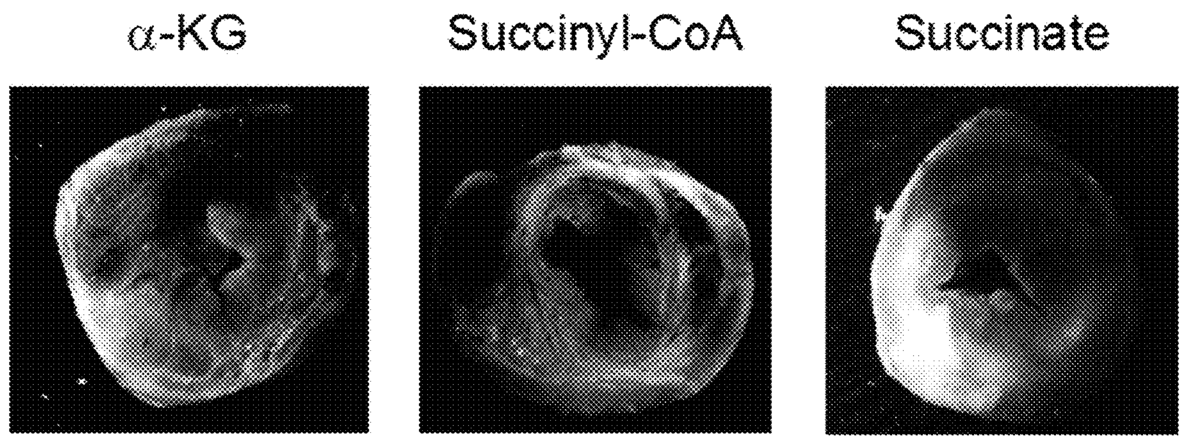
FIG. 13 are representative triphenyl tetrazolium chloride (TTC) stained cross-sections of the heart showing that metabolic conversion of α-KG to succinyl-CoA may contribute to protection. The LAD was occluded for 45 minutes followed by 24 hours of reperfusion. One single IV bolus of α-KG (800 μM), succinyl-CoA (800 μM), or succinate (800 μM) was administered at reperfusion. Infarcted tissue is white, the rest of the area at risk is red, and non-risk tissue is dark blue.

In the cell, α-KG is decarboxylated to succinyl-CoA and $CO_2$ by α-KG dehydrogenase (α-KGDH). Interestingly, it was found that succinyl-CoA exhibits significant protection against IR injury, whereas succinate, which is the next intermediate in the TCA cycle, does not (FIG. 13). These results indicate that succinyl-CoA itself plays an active role in protection and open a new area of investigation into additional therapeutic strategies against IR injury.

Example 6

α-KG Increases Cyclophilin D Binding to Complex V

Mitochondrial membrane permeability transition pore (mPTP) is a structure that forms in the inner membrane of the mitochondria under certain pathological conditions including stroke and myocardial ischemia-reperfusion. Induction of mPTP leads to mitochondrial swelling, loss of membrane potential, and activation of cell death signaling. mPTP consists of Complex V and cyclophilin D (CypD). The opening of mPTP is affected by the binding affinity of CypD to Complex V; increased CypD binding inhibits the induction of mPTP. In some embodiments, studies have shown that mPTP opening can be induced or inhibited by Complex V inhibitors. See e.g., Giorgio, et al. (2013) PNAS USA 110:5887-5892.

Figure 14:
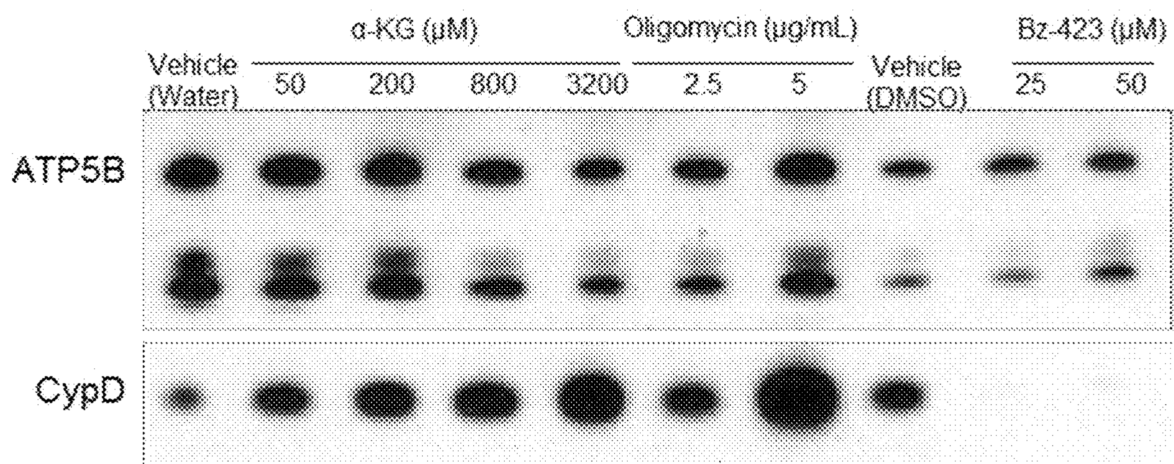
FIG. 14 is an immunoblot illustrating an increase in cyclophilin D binding to Complex V induced by α-KG, which indicates that that α-KB may confer cardioprotection by inhibiting the induction of mPTP opening during reperfusion. Extracts and immunoprecipitates of mouse heart mitochondria using ATP synthase immunoprecipitation kit (Abcam, ab190715) were immunoblotted for ATPSB and CypD. Sample preparation and immunoprecipitation were performed according to manufacturer's standard protocols. α-KG and oligomycin were dissolved in water. Bz-423 was dissolved in DMSO. Water and DMSO were used as respective vehicle controls (water for α-KG and oligomycin set of experiments; and DMSO for the Bz-423 experiments).

As illustrated in Example 3, α-KG inhibits the $F_1$ subunit of Complex V. In this example, it was found that α-KG increased CypD binding to Complex V (FIG. 14). This suggests that α-KG may inhibit the induction of mPTP opening during reperfusion to confer cardioprotection. The known Complex V inhibitor oligomycin (which inhibits the $F_O$ subunit of ComplexV) also increases CypD-Complex V affinity and confers cardioprotection. In contrast, Bz-423, another Complex V inhibitor, reduces CypD affinity to Complex V and induces apoptosis.

All scientific and technical terms used in this application have meanings commonly used in the art unless otherwise specified.

The section headings used herein are for organizational purposes and are not to be construed as limiting the subject matter described.

As used herein, the terms "subject", "patient", and "individual" are used interchangeably to refer to humans and non-human animals. The term "non-human animal" includes all vertebrates, e.g., mammals and non-mammals, such as non-human primates, horses, sheep, dogs, cows, pigs, chickens, and other veterinary subjects and test animals. In some embodiments, the subject is a mammal. In some embodiments, the subject is a human.

The use of the singular can include the plural unless specifically stated otherwise. As used in the specification and the appended claims, the singular forms "a", "an", and "the" can include plural referents unless the context clearly dictates otherwise. The use of "or" can mean "and/or" unless stated otherwise. As used herein, "and/or" means "and" or "or". For example, "A and/or B" means "A, B, or both A and B" and "A, B, C, and/or D" means "A, B, C, D, or a combination thereof" and said "combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method of treating or reducing an ischemia-reperfusion (IR) injury to a tissue in a subject, comprising administering to the subject a therapeutically effective amount of a pharmaceutical composition comprising:

a therapeutically effective amount of a compound of Formula I:

(I)

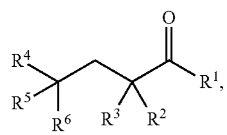

or a salt thereof, wherein:

$R^1$ is hydrogen, halogen, —CHO, —$OR^7$, —$NR^8R^9$, —$COOR^7$, —$CONR^8R^9$, —$SR^{10}$, substituted or unsubstituted alkyl, or substituted or unsubstituted heteroalkyl;

$R^2$ and $R^3$ are each independently hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl;

or $R^2$ and $R^3$, together with the atom to which they are bound, form an oxo;

$R^4$ and $R^5$ are each independently hydrogen, halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl;

$R^6$ is halogen, —CN, —CHO, —$OR^7$, —$NR^8R^9$, —$COOR^7$, —$CONR^8R^9$, —$NO_2$, —$SR^{10}$, substituted or unsubstituted alkyl, or substituted or unsubstituted heteroalkyl; and each $R^7$, $R^8$, $R^9$, and $R^{10}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein each $R^7$ substituent is independently selected when two or more $R^7$ substituents are present, each $R^8$ substituent is independently selected when two or more $R^8$ substituents are present, each $R^9$ substituent is independently selected when two or more $R^9$ substituents are present, and each $R^{10}$ substituent is independently selected when two or more $R^{10}$ substituents are present;

wherein the pharmaceutical composition is administered to the subject and reduces infarct size by about 70% or more.

2. The method of claim 1, wherein $R^1$ is —OH, —O—($C_{1-20}$ substituted alkyl) or —O—($C_{1-20}$ unsubstituted alkyl).

3. The method of claim 2, wherein $R^1$ is —O-(n-octyl).

4. The method of claim 2, wherein $R^1$ is —OH.

5. The method of claim 1, wherein $R^2$ is —$OR^7$ or —$NR^8R^9$.

6. The method of claim 5, wherein $R^2$ is —OH or —$NH_2$.

7. The method of claim 1, wherein $R^3$ is hydrogen.

8. The method of claim 1, wherein $R^2$ and $R^3$, together with the atom to which they are bound, form an oxo.

9. The method of claim 1, wherein $R^4$ and $R^5$ are each independently hydrogen or —$CH_3$.

10. The method of claim 1, wherein $R^6$ is —COOH, —COO—($C_{1-20}$ unsubstituted alkyl), —$CONH_2$, or —CONH—($C_{1-20}$ unsubstituted alkyl).

11. The method of claim 10, wherein $R^6$ is —COOH or —COO-(n-octyl).

12. The method of claim 1, wherein:

$R^1$ is hydrogen, —OH, —O—($C_{1-20}$ substituted alkyl) or —O—($C_{1-20}$ unsubstituted alkyl);

$R^2$ and $R^3$ are each independently hydrogen, —$OR^7$, or —$NR^8R^9$; or $R^2$ and $R^3$ form an oxo together with the atom to which they are bound;

$R^4$ and $R^5$ are each independently hydrogen or —$CH_3$; and $R^6$ is —COOH, —COO—($C_{1-20}$ unsubstituted alkyl), —COO—($C_{1-20}$ substituted alkyl), $CONH_2$, —CONH—($C_{1-20}$ unsubstituted alkyl), or —CONH—($C_{1-20}$ substituted alkyl).

13. The method of claim 12, wherein $R^1$ is —OH and $R^6$ is —COO—($C_{1-20}$ unsubstituted alkyl); or $R^1$ is —O—($C_{1-20}$ unsubstituted alkyl) and $R^6$ is —COOH.

14. The method of claim 1, wherein the compound of Formula I is administered orally.

15. The method of claim 1, wherein the compound of Formula I is administered within 1 to 2 hours of an event that causes IR injury or reperfusion injury.

16. The method of claim 14, wherein the event is a myocardial infarction.

17. The method of claim 1, wherein the compound of Formula I is administered as a single dose.

18. The method of claim 1, wherein the compound of Formula I is administered to the subject in combination with an additional therapeutic agent.

19. The method of claim 18, wherein the additional therapeutic agent is oligomycin or aspirin.

20. The method of claim 1, wherein the tissue is cardiac tissue.

* * * * *